(12) United States Patent
Gupta et al.

(10) Patent No.: US 11,980,386 B2
(45) Date of Patent: May 14, 2024

(54) TISSUE COLLECTION DEVICE FOR CATHETER

(71) Applicant: Avinger, Inc., Redwood City, CA (US)

(72) Inventors: Priyanshu Gupta, Hornsby (AU); Christina Van, San Leandro, CA (US); Nicholas J. Spinelli, San Carlos, CA (US); John B. Simpson, Woodside, CA (US)

(73) Assignee: Avinger, Inc., Redwood City, CA (US)

( * ) Notice: Subject to any disclaimer, the term of this patent is extended or adjusted under 35 U.S.C. 154(b) by 34 days.

(21) Appl. No.: 17/445,648

(22) Filed: Aug. 23, 2021

(65) Prior Publication Data
US 2022/0079617 A1    Mar. 17, 2022

Related U.S. Application Data

(63) Continuation of application No. 14/776,749, filed as application No. PCT/US2013/031978 on Mar. 15, 2013, now Pat. No. 11,096,717.

(51) Int. Cl.
*A61B 17/3207*    (2006.01)
*A61B 10/02*    (2006.01)
*A61B 17/32*    (2006.01)

(52) U.S. Cl.
CPC .. *A61B 17/320783* (2013.01); *A61B 10/0275* (2013.01); *A61B 2017/320064* (2013.01); *A61B 2017/320791* (2013.01)

(58) Field of Classification Search
CPC ........ A61B 10/0275; A61B 17/320783; A61B 2017/320064; A61B 2017/320791;
(Continued)

(56) References Cited

U.S. PATENT DOCUMENTS

| | | |
|---|---|---|
| 3,367,727 A | 2/1968 | Ward et al. |
| 3,908,637 A | 9/1975 | Doroshow |

(Continued)

FOREIGN PATENT DOCUMENTS

| | | |
|---|---|---|
| CN | 1875242 A | 12/2006 |
| CN | 1947652 A | 4/2007 |

(Continued)

OTHER PUBLICATIONS

Simpson et al.; U.S. Appl. No. 17/449,867 entitled "Occlusion-crossing devices, imaging, and atherectomy devices," filed Oct. 4, 2021.
(Continued)

*Primary Examiner* — Jocelin C Tanner
(74) *Attorney, Agent, or Firm* — Shay Glenn LLP

(57) ABSTRACT

Versatile tissue collection devices that can provide reduced crossing profiles, fluid pressure release, and/or easy cleaning or removal. In particular, devices having tissue collection devices with multiple configurations to facilitate navigation through narrow vessel cross-sections while also providing adequate tissue storage capacity. Additionally, the devices may include detachable components that allow easy removal, cleaning, and replacement during a procedure. Furthermore, venting elements and sections may be included to relieve fluid buildup in storage reservoirs.

28 Claims, 26 Drawing Sheets

(58) Field of Classification Search
CPC ...... A61F 2/02; A61F 2/04; A61F 2/06; A61F 2/01; A61F 2/0108; A61F 2/011; A61F 2002/016; A61F 2002/018
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,808,163 A * | 2/1989 | Laub ............... A61M 29/02 606/198 |
| 4,841,977 A | 6/1989 | Griffith et al. |
| 4,842,578 A | 6/1989 | Johnson et al. |
| 4,850,354 A | 7/1989 | Mcgurk-Burleson et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,002,560 A * | 3/1991 | Machold ............... A61F 2/95 606/198 |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A * | 9/1995 | Schmaltz ............... A61F 2/88 606/198 |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunok et al. |
| 5,556,405 A | 9/1996 | Lary |
| 5,607,394 A | 3/1997 | Andersen et al. |
| 5,613,981 A | 3/1997 | Boyle et al. |
| 5,620,426 A | 4/1997 | Braithwaite |
| 5,632,754 A | 5/1997 | Farley et al. |
| 5,632,755 A | 5/1997 | Nordgren et al. |
| 5,667,490 A | 9/1997 | Keith et al. |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A * | 8/1999 | Bates ............... A61B 17/221 606/159 |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |

(56) References Cited

U.S. PATENT DOCUMENTS

| | | |
|---|---|---|
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 * | 1/2004 | Samson ............... A61M 29/02 606/198 |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Teamney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 * | 8/2010 | Besselink ............... A61F 2/013 600/184 |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,244,934 B2 | 4/2019 | Tachibana et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,860,484 B2 | 12/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,076,773 B2 | 8/2021 | Patel et al. |
| 11,096,717 B2 | 8/2021 | Gupta et al. |
| 11,134,849 B2 | 10/2021 | Simpson et al. |
| 11,135,019 B2 | 10/2021 | Spencer et al. |
| 11,147,583 B2 | 10/2021 | Patel et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |

(56) References Cited

U.S. PATENT DOCUMENTS

| | | |
|---|---|---|
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0163085 A1 | 8/2003 | Tanner et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1* | 1/2005 | Bonnette ............... A61F 2/013 606/200 |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2008/0287795 A1 | 11/2008 | Klingensmith et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |

(56) References Cited

U.S. PATENT DOCUMENTS

| | | |
|---|---|---|
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense et al. |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Tearney et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0203230 A1 | 8/2012 | Adams |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0243881 A1* | 8/2014 | Lees .................. A61F 2/01 606/200 |
| 2014/0275996 A1 | 9/2014 | Stigall |
| 2014/0371718 A1 | 12/2014 | Alvarez et al. |
| 2015/0025310 A1 | 1/2015 | Everingham et al. |
| 2015/0141816 A1 | 5/2015 | Gupta et al. |
| 2015/0320975 A1 | 11/2015 | Simpson et al. |
| 2015/0327866 A1* | 11/2015 | Eckhouse .......... A61F 2/844 623/1.15 |
| 2016/0144155 A1 | 5/2016 | Simpson et al. |
| 2017/0100144 A1* | 4/2017 | Zhadkevich ...... A61M 25/1011 |
| 2018/0207417 A1 | 7/2018 | Zung et al. |
| 2019/0021679 A1 | 1/2019 | Christensen |
| 2019/0029714 A1 | 1/2019 | Patel et al. |
| 2019/0110809 A1 | 4/2019 | Rosenthal et al. |
| 2019/0209206 A1 | 7/2019 | Patel et al. |
| 2019/0313941 A1 | 10/2019 | Radjabi |
| 2020/0029801 A1 | 1/2020 | Tachibana et al. |
| 2020/0060718 A1 | 2/2020 | Patel et al. |
| 2020/0069253 A1 | 3/2020 | Black et al. |
| 2020/0315654 A1 | 10/2020 | Patel et al. |
| 2020/0323553 A1 | 10/2020 | Fernandez et al. |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/1077262 | 6/2021 | Spencer et al. |
| 2021/0267621 A1 | 9/2021 | Simpson et al. |
| 2021/0330345 A1 | 10/2021 | Newhauser et al. |
| 2022/0039828 A1 | 2/2022 | Patel et al. |
| 2022/0168011 A1 | 6/2022 | Patel et al. |
| 2022/0273336 A1 | 9/2022 | Fernandez et al. |
| 2022/0273337 A1 | 9/2022 | Patel et al. |
| 2023/0225616 A1 | 7/2023 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |

(56) References Cited

FOREIGN PATENT DOCUMENTS

| | | |
|---|---|---|
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |

OTHER PUBLICATIONS

Spencer et al.; U.S. Appl. No. 17/449,895 entitled "Occlusion-crossing devices, atherectomy devices, and imaging," filed Oct. 4, 2021.
Patel et al.; U.S. Appl. No. 17/455,655 entitled "Atherectomy catheter with shapeable distal tip," filed Nov. 18, 2021.
Tachibana et al.; U.S. Appl. No. 17/645,722 entitled "Atherectomy catheter drive assemblies," filed Dec. 22, 2021.
Black et al.; U.S. Appl. No. 17/652,073 entitled "Optical coherence tomography for biological imaging," filed Feb. 22, 2022.
Patel et al.; U.S. Appl. No. 17/762,815 entitled "Atherectomy catheter with shapeable distal tip," filed Mar. 23, 2022.
Patel et al.; U.S. Appl. No. 17/763,810 entitled "Occlusion-crossing devices," filed Mar. 25, 2022.
Patel et al.; U.S. Appl. No. 17/816,673 entitled "Atherectomy catheter with serrated cutter," filed Aug. 1, 2022.
Aziz et al.; Chronic total occlusions—a stiff challenge requiring a major breakthrough: is there light at the end of the tunnel?; Heart; vol. 91; suppl. III; pp. 42-48; Jun. 2005.
Bayer Material Science: ; Snap-Fit Joints for Plastics; 26 pages; retrieved from the Internet: (https://web.archive.org/web/20121119232733if_/http://fab.cba.mit.edu:80/classes/S62.12/people/vernelle.noel/Plastic_Snap_fit_design.pdf) on Sep. 26, 2018.
Choma et al.; Sensitivity advantage of swept source and fourier domain optical coherence tomography; Optics Express; 11(18); pp. 2183-2189; Sep. 8, 2003.
De Boer et al.; Improved signal-to-noise ratio in spectral-domain compared with time-domain optical coherence tomography; Optics Letters; 28(21); pp. 2067-2069; Nov. 2003.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Han et al.; In situ Frog Retina Imaging Using Common-Path OCT with a Gold-Coated Bare Fiber Probe; CFM6; San Jose, California; CLEO, May 4, 2008; 2 pages.
Leitgeb et al.; Performance of fourier domain vs time domain optical coherence tomography; Optics Express; 11(8); pp. 889-894; Apr. 21, 2003.
Linares et al.; Arbitrary single-mode coupling by tapered and nontapered grin fiber lenses; Applied Optics; vol. 29; No. 28; pp. 4003-4007; Oct. 1, 1990.
Merriam Webster; Proximal (Definition); 10 pages; retrieved from the internet (https://www.merriam-webster.com/dictionary/proximal) on Jun. 9, 2021.
Muller et al.; Time-gated infrared fourier-domain optical coherence tomography; CFM5; San Jose, California; CLEO May 4, 2008; 2 pages.
Rollins et al.; Optimal interferometer designs for optical coherence tomography; Optics Letters; 24(21); pp. 1484-1486; Nov. 1999.
Schmitt et al.; A new rotational thrombectomy catheter: System design and first clinical experiences; Cardiovascular and Interventional Radiology; Springer-Verlag; 22(6); pp. 504-509; Nov. 1, 1999.
Sharma et al.; Common-path optical coherence tomography with side-viewing bare fiber probe for endoscopic optical coherence tomography; Rev. Sci. Instrum.; vol. 78; 113102; 5 pages: Nov. 6, 2007.
Sharma et al.; Optical coherence tomography based on an all-fiber autocorrelator using probe-end reflection as reference; CWJ13; San Francisco, California; CLEO May 16, 2004; 4 pages.
Shinkle et al.; Evaluation of stent placement and outcomes with optical coherence tomography; Interv. Cardiol.; 2(4); pp. 535-543; (manuscript version, 12 pages); Aug. 2010.
Stamper et al.; Plaque characterization with optical coherence tomography. Journal of the American College of Cardiology. 47(8); pp. 69-79; Apr. 18, 2006.
Suparno et al., Light scattering with single-mode fiber collimators; Applied Optics; vol. 33; No. 30; pp. 7200-7205; Oct. 20, 1994.
Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.
Wang et al.; Common-path endoscopic Fourier domain OCT with a reference Michelson interferometer; Proceedings of the SPIE; vol. 7566; pp. 75660L-75660L-7; Jan. 2010.
Wikipedia; Hinge; 4 pages; retrieved from the internet (https://en.wikipedia.org/w/index.php?title=Hinge&oldid=479569345) on Jun. 9, 2021.
Smith et al.; U.S. Appl. No. 17/189,123 entitled "Optical pressure sensor assembly," filed Mar. 1, 2021.

(56) References Cited

OTHER PUBLICATIONS

Kankaria; U.S. Appl. No. 17/209,162 entitled "Optical coherence tomography with graded index fiber for biological imaging," filed Mar. 22, 2021.

Patel et al.; U.S. Appl. No. 17/347,419 entitled "Micro-molded anamorphic reflector lens for image guided therapeutic/diagnostic catheters," filed Jun. 14, 2021.

Patel et al.; U.S. Appl. No. 17/443,398 entitled "Guidewire positioning catheter," filed Jul. 26, 2021.

Rosenthal et al.; U.S. Appl. No. 18/337,852 entitled "Atherectomy catheter with laterally-displaceable tip," filed Jun. 20, 2023.

\* cited by examiner

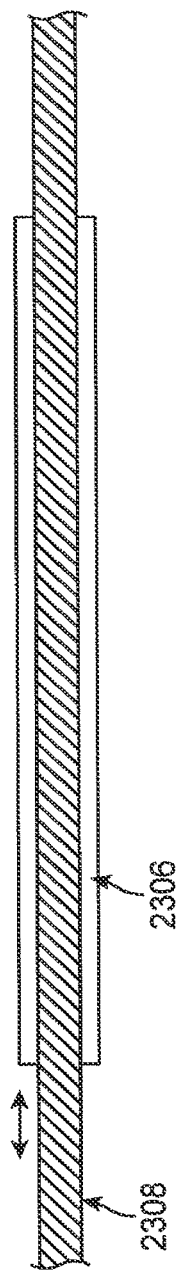

TISSUE COLLECTION DEVICE FOR CATHETER

CROSS REFERENCE TO RELATED APPLICATIONS

This patent application is a continuation of U.S. patent application Ser. No. 14/776,749, filed on Sep. 15, 2015, titled "TISSUE COLLECTION DEVICE FOR CATHETER," now U.S. Pat. No. 11,096,717, which is a U.S. National Phase Application Under 35 U.S.C. § 371 of International Application No. PCT/US2013/031978, filed on Mar. 15, 2013, titled "TISSUE COLLECTION DEVICE FOR CATHETER," now PCT Publication No. WO 2014/142954, each of which is herein incorporated by reference in its entirety.

This application does not claim priority to any other application. This patent application may be related to one or more of the following pending patent applications: U.S. patent application Ser. No. 12/829,277, titled "ATHERECTOMY CATHETER WITH LATERALLY-DISPLACEABLE TIP," filed on Jul. 1, 2010; U.S. patent application Ser. No. 13/175,232, titled "ATHERECTOMY CATHETERS WITH LONGITUDINALLY DISPLACEABLE DRIVE SHAFTS," filed on Jul. 1, 2011; U.S. patent application Ser. No. 13/654,357, titled "ATHERECTOMY CATHETERS AND NON-CONTACT ACTUATION MECHANISM FOR CATHETERS," filed on Oct. 17, 2012; U.S. patent application Ser. No. 13/675,867, titled "OCCLUSION-CROSSING DEVICES, ATHERECTOMY DEVICES, AND IMAGING," filed on Nov. 13, 2012; International Patent Application No. PCT/US2013/031901, titled "ATHERECTOMY CATHETERS WITH IMAGING," filed on Mar. 15, 2015; and International Patent Application No. PCT/US2013/032494, titled "BALLOON ATHERECTOMY CATHETERS WITH IMAGING," filed on Mar. 15, 2015. Each of these references is herein incorporated by reference in its entirety.

INCORPORATION BY REFERENCE

All publications and patent applications mentioned in this specification are herein incorporated by reference in its entirety to the same extent as if each individual publication or patent application was specifically and individually indicated to be incorporated by reference.

FIELD

Described herein are tissue collection devices that can be used with occlusion-crossing devices or systems such as atherectomy catheters. The tissue collection devices described may be configured with one or more of the following features: adjustable crossing profile; easily cleanable or replaceable components; and/or venting elements. Methods of using the tissue collection devices described herein are also provided.

BACKGROUND

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

One way to address this challenge has been the use of atherectomy as a viable primary or adjunctive therapy prior to stenting for the treatment of occlusive coronary artery disease. Atherectomy offers a simple mechanical advantage over alternative therapies. Removing the majority of plaque mass (e.g., debulking) may create a larger initial lumen and dramatically increases the compliance of the arterial wall. As a result, stent deployment is greatly enhanced.

Despite the potential to improve restenosis rates associated with angioplasty and stenting in the coronary and peripheral vasculature, atherectomy is not commonly performed. Traditional atherectomy devices have been plagued by a number of problems, which have severely limited market adoption. For example, available atherectomy devices often provide insufficient tissue collection and removal options during procedures. Typically, the storage capacity of the tissue collection compartment of an atherectomy device is not large enough to accommodate the amount of excised tissue. As such, the device operator must remove the device in order to clean the filled compartment before finishing the procedure. Alternatively, the operator may continue the procedure without collecting the resulting debris, which then leaves the debris in the patient's system to possibly redeposit onto the vessel walls.

Although having a larger storage space would solve this problem, the need for a greater tissue storage capacity is balanced against the necessity for an adequately narrow crossing profile. The tissue storage area often forms the largest crossing profile for the atherectomy device, which results in a larger crossing profile with increased storage capacity. Larger crossing profiles make it difficult for the atherectomy or other occlusion-crossing devices to cross tight vessel regions without damaging or injuring the surrounding vessel tissue. As such, there is a need for a tissue collection device that can satisfy the competing interests of a small crossing profile and a large storage capacity.

Another challenge for atherectomy has been the tendency for collected tissue to form blockages within the collection chambers. Collected debris can seal off sections of the collection reservoir, trapping fluid in storage space. This results in reduced storage capacity as a portion of the chamber is now filled with fluids rather than debris (e.g. plaque) excised from the vessel. The trapped fluids also create fluid pressure resisting the storage of additional material. Atherectomy devices commonly utilize tissue packing devices that compress the stored tissue into the collection chamber to compact as much tissue into the chamber as possible. However, fluid trapped in the collection chamber generates back pressure against the packing device, which prevents optimal use of the storage space. To avoid these concerns, there is a need for a tissue collection device that vents or releases fluids from the storage chamber.

Additionally, tissue removed during atherectomy procedures can still exceed storage capacity regardless of how much storage is provided. Depending on the treatment site, the physician may remove an atherectomy device several times to clean the filled tissue collection chamber. This is often suboptimal as available devices do not have easily detachable collection chambers for quick cleaning. Accordingly, there is a need for a tissue collection device that is configured to be easily removed, replaced, and/or cleaned during a procedure.

In light of the concerns described above, tissue collection devices, chambers, or reservoirs and methods for using these are described herein to address at least some of the challenges illustrated above.

SUMMARY OF THE DISCLOSURE

The present invention relates to intravascular tissue collection devices.

Some embodiments described herein relate to a tissue collection device having a proximal end and a distal end defining a length of the device; a hollow shaft located along at least a portion of said length, the shaft defining a lumen; a tendon member residing in the shaft lumen; and a tissue storage reservoir having an adjustable cross-section.

In some variations, the tissue storage reservoir (which may be defined by a tip portion) is movable between a first configuration and a second configuration, the second configuration having a smaller crossing profile and a reduced cross-section relative to the first configuration. In some embodiment, the tip portion or tissue storage reservoir is configured to compress when moved to the second configuration and expand when moved to the first configuration. Furthermore, the tip portion or tissue storage reservoir may include a mesh that defines the storage reservoir. The mesh may be configured to collapse when the tip portion or tissue storage reservoir is moved from the first configuration to the second configuration. In other embodiments, the tip portion or tissue storage reservoir includes a wire frame that is configured to collapse when the tip portion or tissue storage reservoir moves from the first to the second configuration.

Additionally, the tip portion or tissue storage reservoir may include an elastic material, a resilient material, or a shape-memory material. In some cases, the tissue storage reservoir may be formed from a braided nitinol mesh that is configured to collapse and expand between the first and second configurations.

In any of the preceding embodiments, the tissue storage reservoir is configured to move from the first configuration to the second configuration by applying a distally directed force along a longitudinal axis of the device. In any of the preceding embodiments, the distally directed force is applied to the distal end of the device.

In any of the preceding embodiments, distally moving the tendon member against a distal end of the device applies a distally directed force to thereby move the tissue storage reservoir from a first configuration to a second configuration. In some cases, the tissue storage reservoir has a distal end and a proximal end, the distal end of the reservoir fixed to the tendon member and the proximal end of the reservoir fixed to the hollow shaft. In other variations, the reservoir is adapted to transition to the second configuration by distally moving the tendon member relative to the shaft. In any of the preceding embodiments, proximally moving the tendon member moves the tissue storage reservoir from a second configuration to a first configuration. In any of the preceding variations, the reservoir is adapted to transition to the second configuration by rotating the reservoir about the shaft to form a coiled collapsed configuration. In any of the preceding embodiments, the tissue storage reservoir includes a resilient frame configured to naturally return to the first configuration.

In any of the preceding embodiments, the tissue storage reservoir is configured to move from the first configuration to the second configuration by extending the length of the device.

Additionally, in any of the preceding embodiment, the device may include a guidewire lumen and a guidewire residing in a guidewire lumen, wherein distally moving the guidewire against the distal end of the device applies a distally directed force to thereby move the tissue storage reservoir from a first configuration to a second configuration. In any of the preceding embodiments, the tissue storage reservoir is configured to return to the first configuration from the second configuration after the distal force is released. In any of the preceding embodiments, the tissue storage reservoir is configured to return to the first configuration from the second configuration by applying a proximally directed force to the distal end.

In any of the preceding embodiments, the first configuration may have a crossing profile of about 0.080 inches. In any of the preceding embodiments, the second configuration may have a crossing profile of about 0.020 inches. In any of the preceding embodiments, the crossing profile of the tissue storage reservoir is between about 0.020 inches to about 0.080 inches.

Additionally, in any of the preceding embodiments, the proximal end of the device may be adapted to couple to a catheter.

In any of the preceding embodiments, the device length is between about 10 mm to about 100 mm.

In any of the preceding embodiments, the tissue collection device may include a tissue storage reservoir having a plurality of gaps having a width between about 50 μm to about 200 μm. In any of the preceding embodiments, the tissue storage reservoir may include a porous member configured allow fluid movement out of the storage reservoir. In any of the preceding embodiments, the tissue storage reservoir includes a plurality of gaps of between about 0.01 to about 0.5 mm.

In any of the preceding embodiments, the devices include a third configuration, the third configuration having a greater crossing profile relative to the first configuration.

In any of the preceding embodiments, the tissue storage reservoir is adapted to be biased towards the first configuration.

Further embodiments provide for an atherectomy catheter device having an elongate body; a central lumen extending within the elongate body from a proximal end of the elongate body to a distal end of the elongate body; a rotatable cutter at the distal end of the elongate body and configured to rotate relative to the elongate body; and a tissue collection device positioned at the distal end of the elongate body, distal of the rotatable cutter, the tissue collection device including a tissue storage reservoir, wherein the tissue collection device has an adjustable crossing profile.

In any of the preceding embodiments, the tissue collection device includes a plurality of configurations, a first configuration having a smaller crossing profile and a reduced storage capacity relative to a second configuration. In other embodiments, the atherectomy device has a crossing profile that is adjustable by varying the length of the tissue collection device or the tissue storage reservoir. In further variations, the atherectomy device is configured for shortening the length of the tissue collection device to increase the crossing profile. In any of the preceding embodiments, the tip portion can include a braided mesh defining the storage reservoir.

Other embodiments provide for a tissue collection device including a proximal end and a distal end defining a length of the device; and a tissue storage reservoir. The tissue storage reservoir includes a venting element configured to release fluid pressure in the storage reservoir. In some embodiments, the venting element includes a plurality of apertures on the tip portion. In further variations, the venting element includes a mesh material.

In any of the preceding embodiments, the device (e.g. tip portion) may include a plurality of venting sections configured to allow fluid movement out of the storage reservoir. In any of the preceding embodiments, the venting element is positioned adjacent the distal end of the device.

Further embodiments provide for an atherectomy device including an elongate body; a central lumen extending within the elongate body from a proximal end of the elongate body to a distal end of the elongate body; a rotatable cutter at the distal end of the elongate body and configured to rotate relative to the elongate body; and a tissue collection device positioned at the distal end of the elongate body, distal of the rotatable cutter. In any of the preceding embodiments, the tissue collection device includes a tip portion defining a tissue storage reservoir. In some embodiments, the tip portion may include a venting element configured to release fluid pressure in the storage reservoir.

Some embodiments provide a detachable tissue collection device having a tip portion having a first housing and a second housing, the first housing adapted to mechanically couple to the second housing to form the tip portion; and a tissue storage reservoir defined by the tip portion, wherein at least a section of the storage reservoir is configured to be detachable by uncoupling the first housing from the second housing.

In any of the preceding embodiments, the first housing may be configured to couple to the second housing through a mated fit. In any of the preceding embodiments, substantially the entire tissue storage reservoir is detachable by uncoupling the first and second housings. In any of the preceding embodiments, the first housing includes a plurality of angled tabs and the second housing includes a plurality of slots for receiving the plurality of angled tabs to retain the first housing when the angled tabs are engaged with the slots. In any of the preceding embodiments, the angled tabs are formed from a wall of the first housing. In any of the preceding embodiments, the first housing and the second housing are laterally locked when mechanically coupled.

Additionally, any of the preceding embodiments may include a guidewire lumen defined by a first channel on the first housing and a second channel on the second housing. In some embodiments, the first housing and second housing are rotationally locked when a guidewire is placed through the first and second channels.

Other embodiments provide for methods of performing an atherectomy. These methods include collapsing a distal tip region of an atherectomy catheter to a collapsed configuration by applying a distally directed force to the distal tip region; expanding the distal tip region to an expanded configuration by releasing the distally directed force, wherein the expanded configuration has a larger crossing profile and cross-section relative to the collapsed configuration; and storing excised tissue in a tissue storage reservoir of the expanded distal tip region. In any of the preceding embodiments, the storing step includes deflecting the excised tissue into the tissue storage reservoir. In any of the preceding embodiments, the methods may include packing the tissue into the storage reservoir.

Further embodiments provide methods of performing an atherectomy including the steps of packing excised tissue into a storage reservoir defined by the distal tip region of an atherectomy catheter; and ventilating the storage reservoir to reduce back pressure in the storage reservoir.

In any of the preceding embodiments, methods of performing an atherectomy include the steps of detaching a portion of a distal tip region of an atherectomy catheter; and replacing the portion of the distal tip region.

Other embodiments provide for a detachable tissue collection device including a proximal end adapted to releasably couple to a distal end of an atherectomy catheter; a replaceable distal tissue storage reservoir configured to be removable from the atherectomy catheter by uncoupling the proximal end from the distal end of the catheter. In any of the preceding embodiments, the tissue collection device may include a first mating structure at the proximal end configured to couple to a second mating structure on the distal end of the catheter. In any of the preceding embodiments, the first mating structure may include a plurality of projecting tabs and the second mating structure may include a plurality of slots.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 23a-c shows an alternative collapsible tissue collection device.

DETAILED DESCRIPTION

Figure 1:
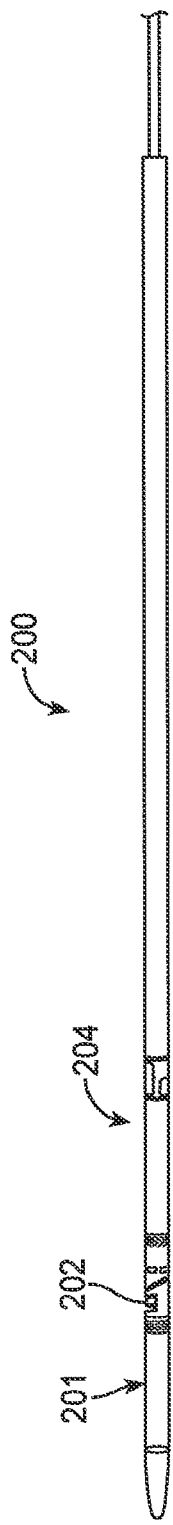
FIG. 1 is a side view of an atherectomy catheter having a distal tissue collection chamber.

The tissue collection devices described herein typically include a tissue chamber, reservoir, and/or tissue storage area adapted for receiving and retaining excised tissue or solid biological material. Advantageously, such collection devices can be used during minimally invasive procedures where tissue or other material is cut and removed from the patient's body. The tissue collection devices may be used with any suitable catheters including, at least, those described in U.S. Patent Application No. 61/646,843, titled "ATHERECTOMY CATHETERS WITH IMAGING," filed on May 14, 2012, U.S. patent application Ser. No. 13/433,049, titled "OCCLUSION-CROSSING DEVICES, IMAGING, AND ATHERECTOMY DEVICES," filed Mar. 28, 2012, U.S. patent application Ser. No. 13/175,232, titled "ATHERECTOMY CATHETERS WITH LONGITUDINALLY DISPLACEABLE DRIVE SHAFTS," filed on Jul. 1, 2011, U.S. patent application Ser. No. 12/829,277, titled "ATHERECTOMY CATHETER WITH LATERALLY-DISPLACEABLE TIP," filed on Jul. 1, 2010, and U.S. patent application Ser. No. 12/829,267, titled "CATHETER-BASED OFF-AXIS OPTICAL COHERENCE TOMOGRAPHY IMAGING SYSTEM," filed on Jul. 1, 2010.

As an initial matter, embodiments described as being on a distal or proximal region of another device (e.g. catheter) are not meant to limit the tissue collection device to any particular location or position. Rather, the described embodiments illustrate examples of how the contemplated tissue collection devices can be used with other devices or systems. Likewise, in some embodiments, the tissue collection devices may be described as having one or more specific features such as detachability or size adjustment. However, it is to be appreciated that the contemplated embodiments may include features in different combinations or variations than the examples provided. For example, some devices may be detachable and size adjustable or only detachable.

As discussed above, a challenge to using atherectomy or, more generally, occlusion-crossing devices, has been the difficulty in storing excised material such as plaque for removal from the patient. A large tissue storage volume often necessitates a large crossing profile to accommodate the storage capacity. To address this problem, one aspect of the invention provides for tissue storage or collection devices with adjustable dimensions. In some embodiments, the devices are designed to change one or more of cross-sectional size, length, inner diameter, outer diameter, etc. to allow the tissue storage device to move between collapsed and expanded configurations.

In such embodiments, the tissue collection device may employ a collapsed or compressed cross-section during insertion into the patient or navigation through narrow vessel sections. Once desired positioning is achieved, the tissue collection device may be expanded to increase the cross-section and crossing profile of the device.

In some cases, the tissue collection device may include a plurality of configurations ranging from a fully collapsed to a fully expanded configuration. For example, at the fully collapsed configuration, the device may have a minimum inner diameter and outer diameter. Likewise, at the fully expanded configuration, the device may have maximum inner and outer diameters. Additionally, beyond the fully collapsed or expanded positions, the tissue device may have configurations with dimensions between maximum and minimum dimensions. Advantageously, this provides the physician with a plurality of configurations within a preset range.

To transition between configurations, the tissue collection device may adjust cross-sectional size and/or the crossing profile by changing the length of the device or a portion of the device. For example, in some embodiments, the device has a length adjustable portion (e.g., an adjustable tip portion) that contains the storage reservoir. The crossing profile around the storage reservoir is reduced by lengthening it (e.g., by lengthening the tip portion). In some cases, applying a distally directed force at the distal end of the storage reservoir and/or tip portion pushes the distal end to extend or elongate the storage reservoir and/or tip portion. Elongating the tip portion, consequently, also compresses the cross-section of the tissue storage reservoir contained within the tip portion to reduce the crossing profile of the device. Lengthening the tip portion/tissue reservoir, therefore, is a means for transitioning the tissue collection device from a first expanded state to a second collapsed state.

Once the distally directed force is released, the tip portion/storage reservoir may return to an expanded position. In some embodiments, the device is biased toward the expanded state whereby releasing the lengthening force allows the tissue storage reservoir to return unassisted to its expanded position. For example, the storage reservoir may be made from a resilient or elastic material or frame with a natural elasticity that springs, recoils, or recovers to the expanded shape once the elongating force is removed or released.

It should be noted that, as used herein, the tip portion may refer to and/or include the storage reservoir. The tip portion (and/or storage reservoir) is not limited to the distal tip region of the devices described herein; additional structures may be located at the distal (or in some orientations, proximal) tip regions. Further, the storage reservoir and/or tip portion may be located proximally of the distal tip of the device(s) described herein.

Alternatively, in another embodiment, the device may require an assisting force to transition from the collapsed to expanded state. In such cases, a force may be applied to transition the collapsed device (e.g., tip portion and/or tissue reservoir) from the elongated configuration to the original expanded configuration. This, in turn, also increases the collapsed crossing profile to the expanded crossing profile. In some variations, this may be achieved by applying a proximal directed force that shortens the elongated tissue storage reservoir. The proximally directed force pulls the distal end of the elongated tip portion back towards the expanded configuration. This causes the outer diameter and crossing profile of the tissue storage reservoir to increase.

A force applying element may be employed to impart force to the device. A tether, tendon member, guidewire, tensioning element, or any other suitable mechanism can be used for this purpose. For example, some embodiments include a hollow shaft or lumen through which an elongate tendon member (e.g., wire) extends. A portion of the tendon member is attached to the tissue device such that moving the tendon member through the lumen imparts a configuration changing force to the device. In some variations, a separate tendon and tendon lumen are not necessary where a guidewire and corresponding guidewire lumen can serve the same function. For example, a guidewire may be received and retained in a guidewire lumen of the tissue collection device such that the guidewire can maneuver the device into various configurations.

Referring now to FIG. 1, a general non-collapsible atherectomy catheter device 200 is shown having a cutter 202 and distal tip region 201 with a tissue storage reservoir. In some variations, the tissue storage reservoir is in the main body 204 of the catheter. However, for illustration purposes, a distal tip storage reservoir is described.

The distal tip region may be hollow or otherwise configured to hold material cut by the atherectomy device. In some variations the distal tip region is clear or at least partially transparent, allowing one to see if material has been collected or remains in the tip region. The distal tip region may include a flush port or may otherwise be adapted to allow removal of cut material stored therein. For example, the distal end may be tapered but may be open. The distal tip region may be removable and/or replaceable. A reusable locking mechanism, such as threads, or the like, may be used to secure a distal tip region on the catheter.

In operation, the distal tip region 201 is advanced into the patient's vasculature and maneuvered to a target treatment location. During advancement, the distal tip region must cross through vessel lesions or narrow/tortuous pathways to position the cutter 202 at a target site for tissue excision. To do so, the crossing profile of the distal tip region 201 must be sized to allow bypass through tight vessel cross-sections.

Additionally, the distal tip region 201 also serves as the tissue collection chamber for storing tissue removed by the cutter 202. At a target site, the cutter 202 may excise the tissue and direct the tissue into a hollow reservoir inside the distal tip region 201. Any number of methods for doing so have been described in the applications aforementioned and incorporated by reference. For example, the cutter 202 may have a scoop shape to cut and deflect tissue into a receiving collection chamber in the distal tip region 201. FIG. 1 shows the distal tip region 201 having a closed nosecone construction with an opening at a proximal end for receiving cut tissue. The structure is relatively inelastic and does not easily compress or change shape. As such, the crossing profile is preset and is not easily changed without permanently deforming and, possibly, damaging the nosecone.

Figure 2:
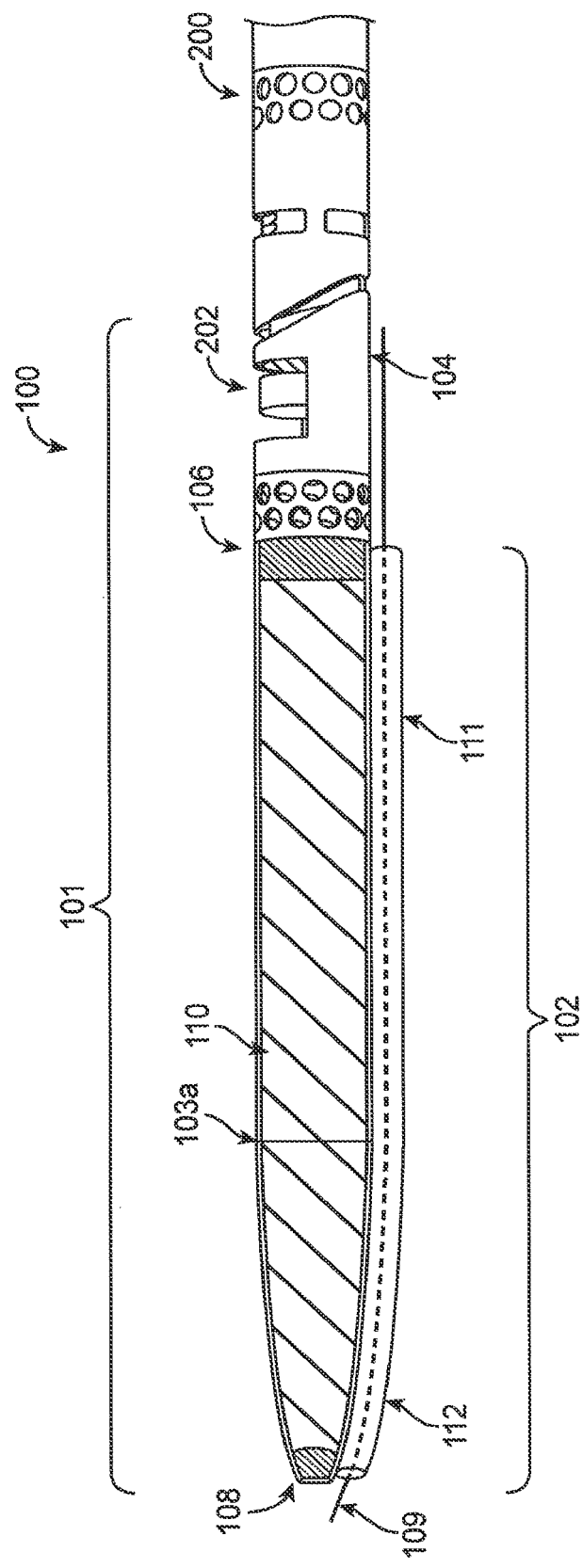
FIG. 2 is a side view of a collapsible tissue collection device attached to a catheter.

FIG. 2 shows a collapsible tissue collection device 100 attached in the distal region 101 of the catheter 200. The tissue collection device 100 includes a proximal housing 104 that attaches the device 100 to the catheter body. In some cases, the proximal housing 104 releasably couples the tissue collection device 100 to the main catheter body through any suitable mechanical attachment means such as friction fit, mated fit, threads, etc. In other embodiments, the proximal housing 104 permanently secures the tissue collection device 100 to the catheter 200.

As shown, the tissue collection device 100 has a size adjustable tip portion or tip 102. The tip portion 102 may also be attached to the proximal housing 104 at a proximal end 106 of the tip portion 102. The tip portion 102 includes a distal end 108 and a length of the device 100 between the two ends 106, 108. A storage reservoir 110 is contained within the tip portion 102. The tissue reservoir 110 may extend along a part of or all of the tip portion. Where the storage reservoir 110 extends to the distal end 108 of the tip portion 102, the distal end may be sealed to prevent the release of tissue from the reservoir. Unlike the distal end 108, the proximal end 106 does not need to be sealed and can include an opening in communication with the tissue storage reservoir. This allows excised tissue to enter the reservoir through the proximal end 106. In some variations, the tissue storage reservoir is attached to the proximal end 106 and the distal end 108 of the tip portion by way of an adhesive or biocompatible polymer such as PEBAX®, Tecothane®, or polyimide. For example, the structure of the reservoir may be fused to a polymer-based housing at the ends 106, 108.

Figure 3:
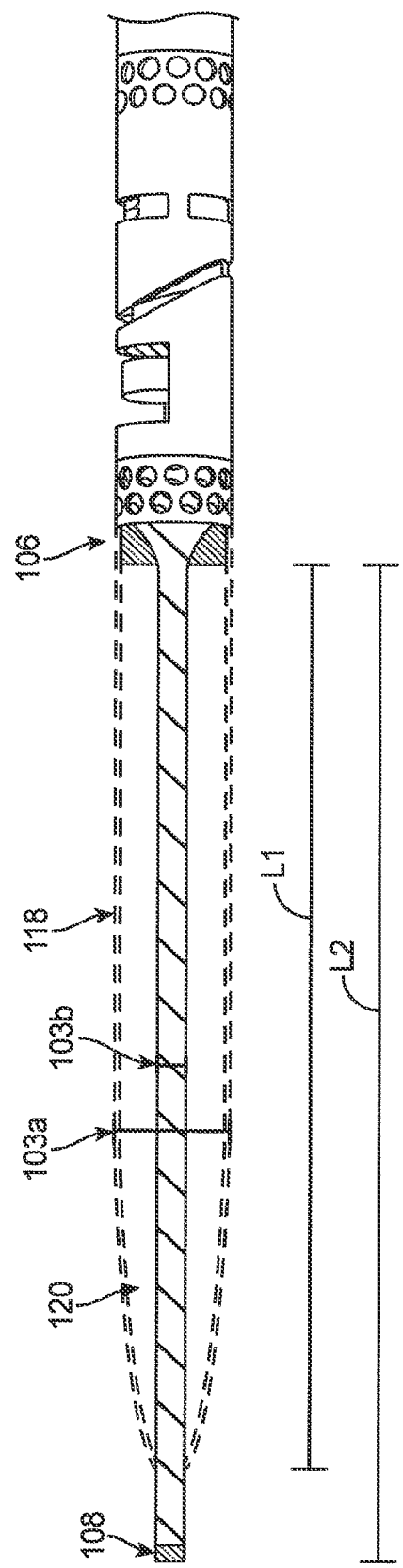
FIG. 3 is a side view of the tissue collection device of FIG. 2 in a collapsed configuration.

FIGS. 2-3 show the collapsible tissue collection device 100 in expanded and collapsed states respectively. In the expanded state, the tissue collection device 100 has a larger crossing profile 103a relative to a collapsed configuration (collapsed crossing profile 103b shown in FIG. 3). By varying the cross-sectional size of the tissue reservoir, the device 100 can assume a reduced profile to navigate through narrow vessel structures.

In order to accommodate dimension changes, the tip portion 102 and/or the storage reservoir 110 may be made from an elastic, deformable, stretchable, or resilient structure or material. Suitable materials include biocompatible shape memory materials, alloys, metals, composites, polymers, etc. These include, but are not limited to, nitinol, PEBAX®, polyimide, PEEK, polyester, polypropylene, Tecothane®, stainless steel, elgiloy, cobalt-chromium alloys, carbon fiber, nylon, titanium and its alloys, or Kevlar. In some embodiments, the material(s) forming the tissue portion/reservoir has a natural elasticity or resilience that biases the material to a relaxed shape. When deformed, the material exhibits a tendency to recover the relaxed shape. Additionally, any biocompatible material may be used that retains collected solids while allowing fluid movement out of the reservoir.

Figure 6:
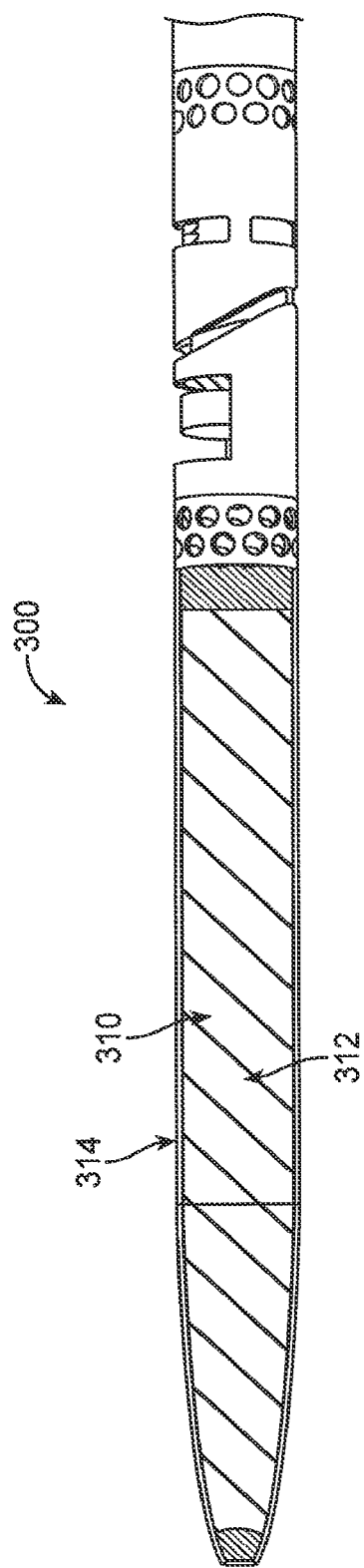
FIG. 6 is a side view of a collapsible tissue collection device with a collapsible frame supporting the tissue storage reservoir.

In some embodiments, the tissue reservoir is defined by a collapsible or foldable structure. This includes a compressible frame that allows the storage reservoir to reduce cross-sectional size. For example, the storage reservoir or tip portion may be constructed from a collapsible frame that supports an unstructured elastic or deformable material. The frame may provide an outer structure or skeleton upon which a deformable material (e.g. flexible mesh) is draped and secured. FIG. 6 shows device 300 with a frame 314 supporting an elastic material 312. The frame defines the outer boundaries of the tissue storage reservoir 310 while the elastic material 312 forms a sheath over the frame 314. The frame 314 is collapsible or foldable while providing support to the elastic material 312. The frame may also include additional support members such as struts, ribs, posts, joints, etc. to facilitate the configuration changes of the tissue collection device.

In some embodiments, the collapsible frame is a network forming a mesh or netted structure. A mesh frame may be braided or woven to increase strength and to better hold stored contents in the collection chamber. Moreover, a wire mesh or netted frame may surround and define the storage reservoir inside the frame.

FIG. 2 shows an example of a mesh structure forming the tissue reservoir on the tip portion 102. The mesh surrounds and defines the storage volume in the storage reservoir 110. As shown, the mesh is attached to the distal and proximal ends of the tip portion. Any attachments means may be used, including fusing the mesh to the ends using a melted polymer such as PEBAX®. In some cases, the mesh is also attached to the housing 104 for additional stability.

In some variations, the mesh is a braided wire that includes gaps and openings. The braid is structured such that gaps are sufficiently small to prevent the release of collected tissue from the storage reservoir. In some embodiments, the gaps are about 0.25 sq cm. In other embodiments, the gaps are between about 50 µm to about 200 µm in width. In other embodiments, the gaps are about 0.01 to about 0.5 mm in width.

Figure 4:
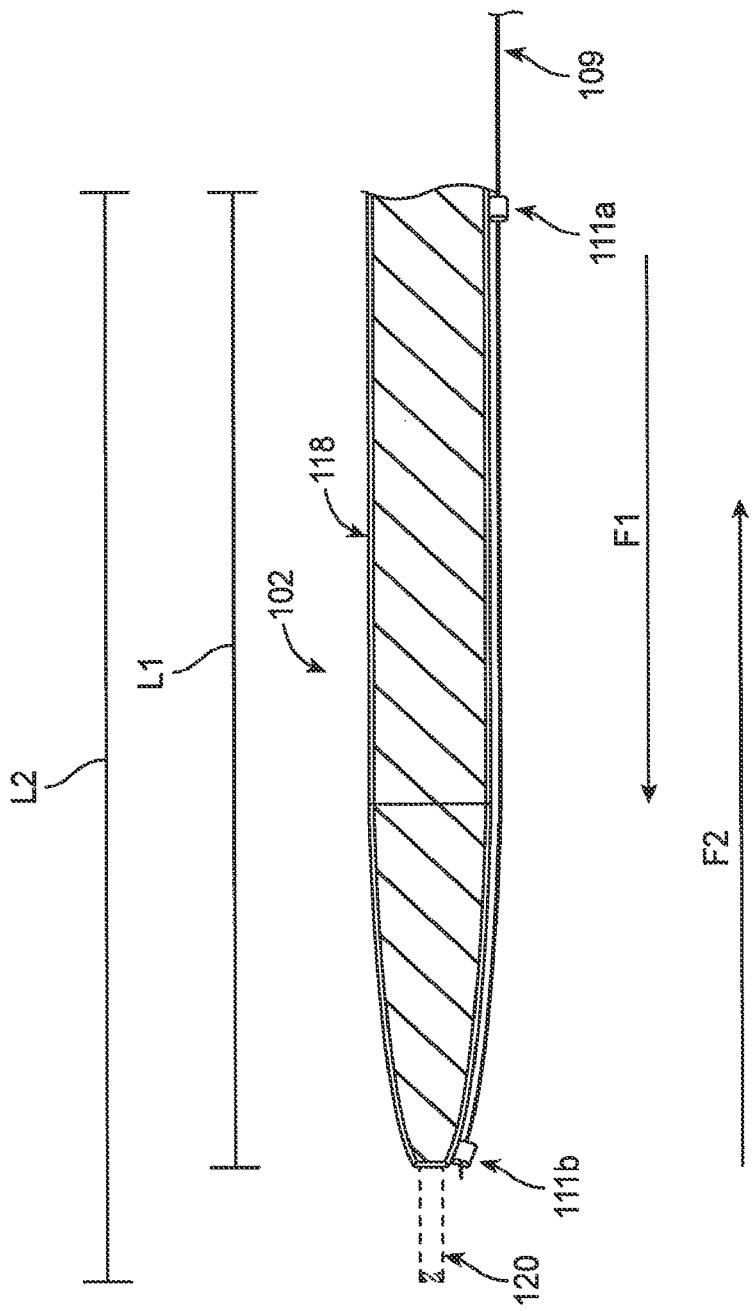
FIG. 4 is a side view of the tissue collection device with varying lengths in different configurations.

Referring now to FIGS. 3-4, the process and mechanism for expanding and collapsing a tissue collection device is described in greater detail. FIG. 3 shows the tissue collection device 100 of FIG. 2 in a reduced crossing profile configuration 120. The tip portion 102 is collapsed to reduce the cross-section of the storage reservoir. The phantom lines indicate the expanded configuration 118 relative to the shown collapsed configuration 120. The crossing profile 103a of the expanded configuration 118 is greater than the crossing profile 103b of the collapsed configuration. Additionally, FIG. 3 shows that the collapsed configuration 120 also exhibits a greater tip portion/storage reservoir length L2 relative to the length L1 of the expanded configuration 118. In this embodiment, extending or elongating the tip portion 102 and tissue storage reservoir 110 reduces the crossing profile.

One method of extending the length of the tip portion or storage reservoir 110 is to apply a distally directed force to the tip portion. This force can be applied along the length of the device or at the distal end 108. In operation, applying a distally directed force (F1) along the longitudinal axis of the tip portion 102 forces the tip portion to lengthen. When the tip portion is stretched or extended, the cross-section of the tip portion compresses to accommodate the tip portion elongation. This reduces the crossing profile of the tissue storage reservoir 110.

Where a collapsible or foldable frame forms the tissue storage reservoir, the distally directed force may transition the tissue collection device from an unfolded to a folded configuration. Referring to FIG. 6, the foldable outer frame 314 may include joints and ribs that pivot or move to reduce crossing profile when a distally directed force is applied.

Alternatively, where a flexible braided mesh (see FIG. 2) forms the reservoir, the braided mesh may accommodate stretching in one or more directions. As shown in FIGS. 2-3, the mesh stretches in the longitudinal direction under the distally directed force. This allows the tissue reservoir to elongate while reducing the mesh's cross-section.

Returning the tissue reservoir to a larger crossing profile from the collapsed configuration can be achieved in several ways. In a first variation, the tissue collection device 100 can return to its expanded state without applying any assisting force to transition the device. This can be accomplished by using a resilient or elastic material for the tissue storage reservoir. For example, the mesh material in FIG. 2 may be biased toward the larger crossing profile configuration such that once the elongating force (F1) is removed, the mesh will recover its natural shape. For this purpose, any resilient material can be used whereby the material has a natural elasticity or tendency to return to an expanded state once the compressing force is no longer applied.

In a second variation, the tissue collection device is not biased toward any particular configuration (e.g. relaxed expanded state). Instead, the material and/or structure forming the tissue storage reservoir remains in the reduced profile configuration even after the elongating force (F1) is no longer applied to the device. In such cases, a proximally directed force (F2) may be required to pull the tip portion into a non-collapsed configuration. In other words, an assisting force is needed to transition the compressed tissue reservoir to an expanded state with a larger crossing profile.

Figure 24:
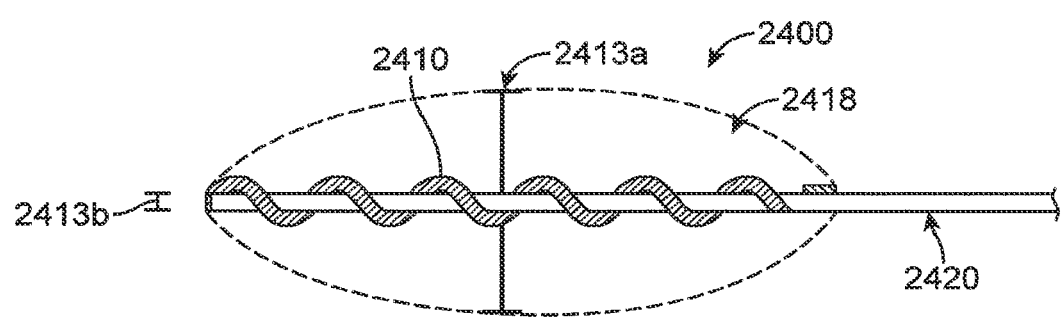
FIG. 24 shows a coiled collapsed configuration for a tissue collection device.
Figure 25:
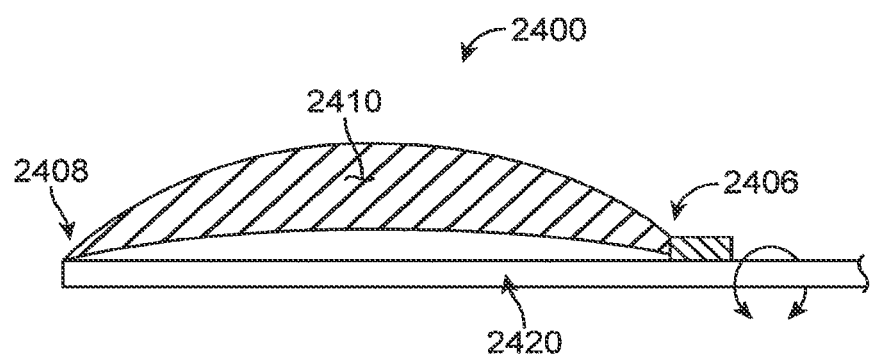
FIG. 25 shows an uncoiled configuration for the device of FIG. 24.

Referring to FIGS. 24-25, an alternative process and mechanism for collapsing and expanding the tissue collection device is shown. The device 2400 includes a storage reservoir 2410 at a tip portion of the device 2400. The expanded state 2418 for device 2400 is indicated by the dotted lines. In the reduced crossing profile configuration shown, the tissue storage reservoir 2140 is wrapped around a shaft 2420 on the device 2400. In some variations, the storage reservoir 2410 is a loose braided mesh that can coil around the shaft 2420. In some embodiments, the structure 2420 is a catheter, guidewire lumen, tendon member lumen, or other housing encircled by the storage reservoir.

To maneuver the device 2400 from the expanded configuration 2418 to the coiled collapsed configuration, the storage reservoir 2410 is rotated or turned about the shaft 2420. In some embodiments, the distal end 2408 of the storage reservoir is fixed to the shaft 2420 and the proximal end 2406 of the reservoir moves about the shaft 2420. Rotating the proximal end 2406 about the shaft 2420 coils the reservoir. In some variations, the storage reservoir is first elongated and then coiled. Elongation can slightly compress the cross-section of reservoir to facilitate the coiling.

For any of the described embodiments, any number of means or mechanisms can be used to apply a collapsing, expanding, or coiling force. FIG. 4 shows the distally or proximally directed force applied by the tendon wire 109. The tendon wire 109 resides in a lumen that is defined, in part or whole, by a tendon housing. FIG. 4 shows the housing in two parts. The first part 111a is at the proximal end and the second part 111*b* is at the distal end. The tendon member 109 is fed through an opening at each of the two-part housing components 111*a-b*. The tendon member 109 is exposed along a length of the tip portion 102 between the two housing components 111*a-b*.

To impart force, the housing components may be constructed to retain the tendon member 109 during configuration changes. For example, the distal housing component 111*b* may include adhesive, stays, stops, or a tight fit such that the housing component resists distal movement of the tendon member 109. In some variations, the tendon member is fixed or fused to the distal end of the tip portion or the tissue storage reservoir. In such cases, distally pushing the tendon member 109 against the distal housing component 111*b* imparts a distally directed force F1 to the distal end of the tip portion 102. This, in turn, pushes the tip portion distally to lengthen the device 100 and reduce the crossing profile.

Additionally, the tendon housing 111 may include adhesive, stays, stops, or fitting dimensions to retain the tendon member while a proximally directed force F2 is applied to pull the distal end of the tip portion proximally. This is applicable, for example, where the tissue storage reservoir does not naturally recover to the expanded state when the collapsing force (F1) is removed. The proximal force (F2) transitions the collapsed configuration back to the expanded state 118.

Figure 5:
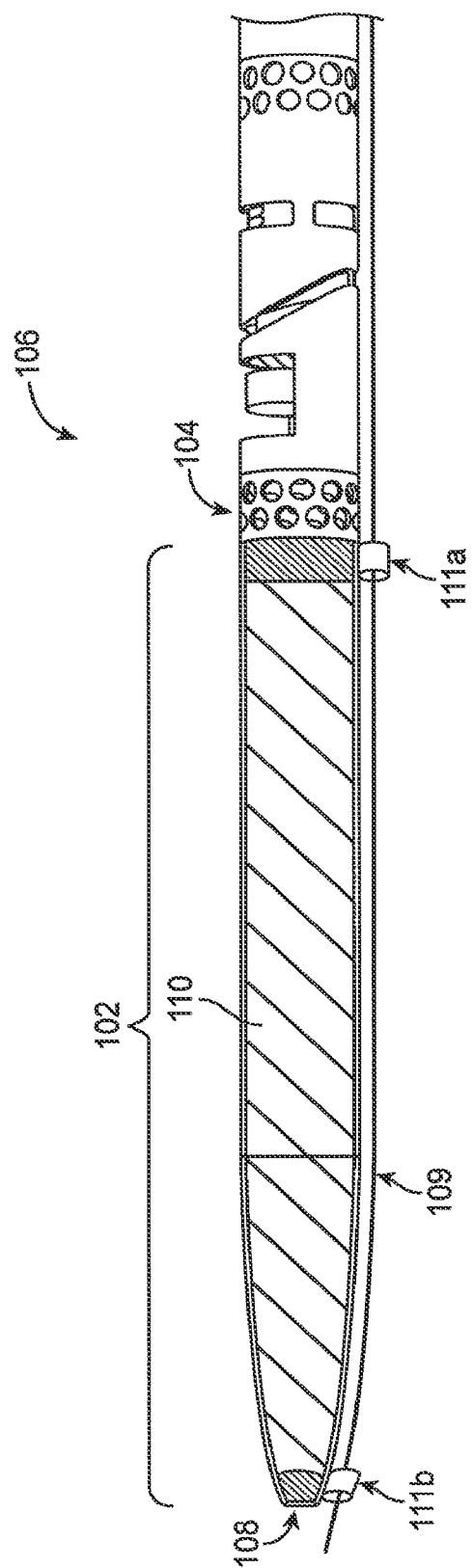
FIG. 5 is a side view of another embodiment of a collapsible tissue collection device including a two-part guidewire housing.

FIGS. 2, 5, and 23*a-c* show various tendon member and housing variations. FIG. 2 shows a lumen 112 along a length or a longitudinal axis of the tissue collection device 100. The lumen 112 is defined by a housing 111 that is also positioned along a length of the device 100. The housing 111 is fixed to the proximal end 106, distal end 108, and along a length of the tip portion 102. A tendon member 109 resides in the lumen 112. FIG. 5 shows a similar arrangement with the housing having two components at the distal and proximal ends. Housing components 111*a-b* define a portion of the lumen where a tendon member is exposed in the area between the housing components.

Although both embodiments, and variations thereof, are suitable, the housing 111 in FIG. 2 may be made from an elastic material that can also elongate. For example, the housing 111 may also be made from a mesh or wire net that can compress and elongate during configuration changes of the storage reservoir.

Figure 23A:
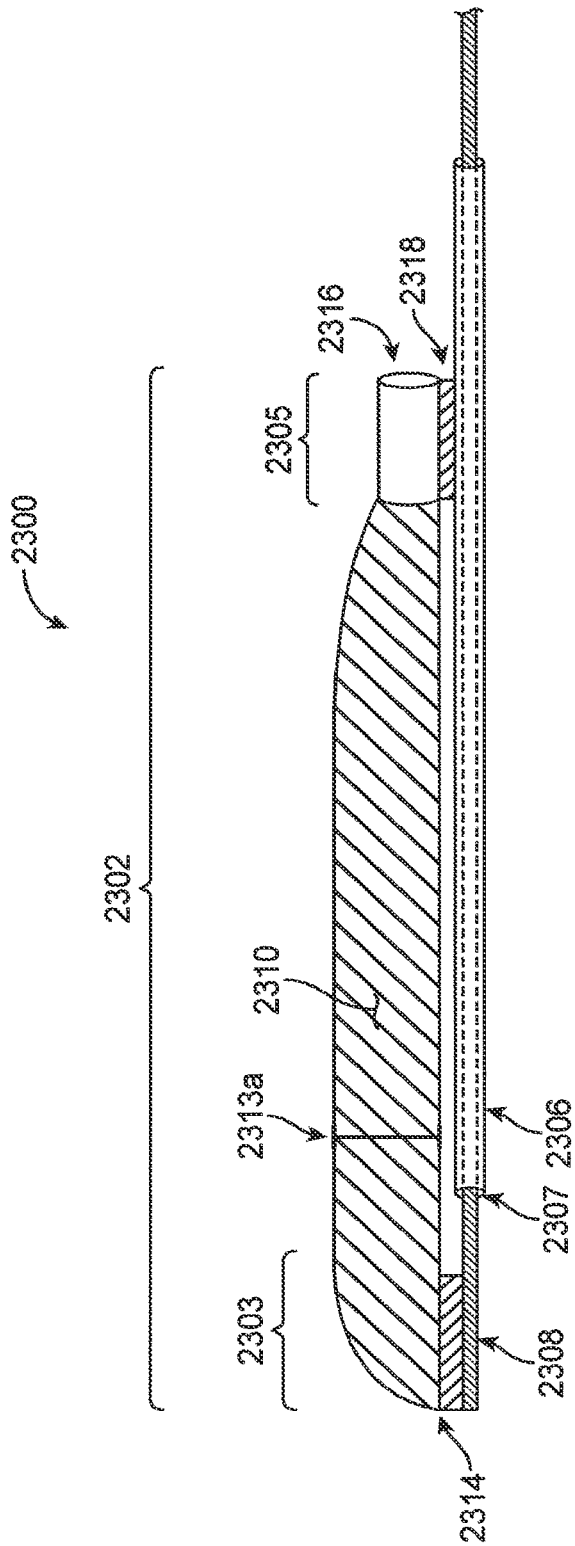
Figure 23C:
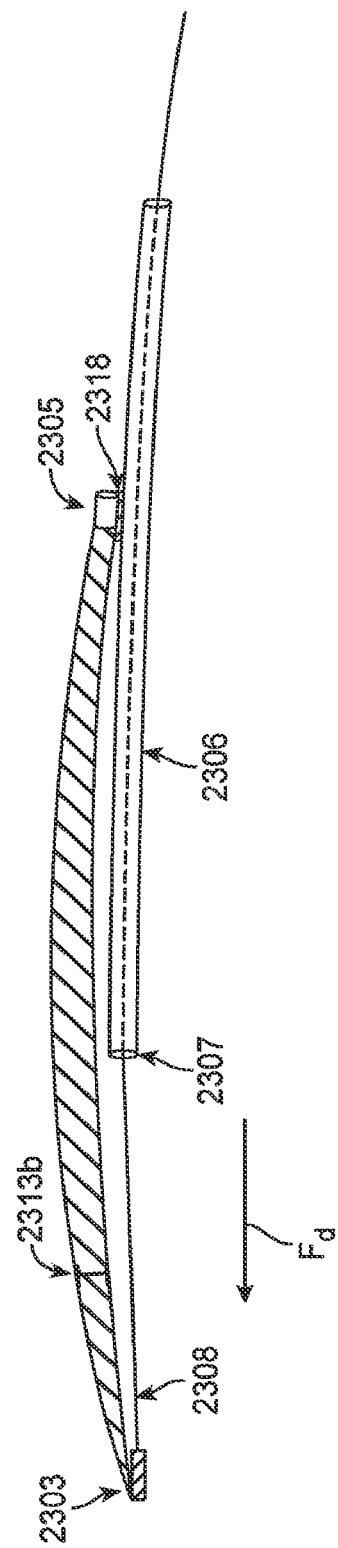

FIGS. 23*a-c* illustrates another alternative housing and tendon member arrangement. Tissue collection device 2300 has a tissue storage reservoir 2310 having a distal end 2303 and a proximal end 2305. At the distal end 2303 the reservoir 2310 is fixed to the tendon member 2308 by an adhesive material 2314 (e.g. a melted and fused polymer). At the proximal end 2305, the reservoir 2310 is fixed to the tendon lumen housing 2306 by an adhesive material 2318 (e.g. a melted and fused polymer). The proximal end 2305 includes an opening 2316 for the excised tissue to be advanced into the reservoir 2310. As shown, the housing 2306 forms a sleeve with an inner lumen 2307 and the tendon member 2308 resides in the lumen 2307. The tendon member 2308 slides or moves longitudinally within lumen 2307. (See FIG. 23*b* showing a cross-section of the housing and tendon member.)

In this embodiment, the device 2400 can be collapsed in a couple of ways. In one variation, the tendon member 2308 is moved distally through the housing 2306 or lumen 2307. This distal movement applies a distal force Fd against the distal tip 2303 of the storage reservoir 2310. Because the proximal end 2305 of the reservoir is fixed to the housing 2306, the distal force Fd pushes against the distal tip 2303 to lengthen the reservoir 2310. This compresses the cross-section and results in the reduced crossing profile 2313*b*. In another variation, the reservoir may be partially elongated before rotating the proximal end 2305 of the reservoir about the housing 2306. This twists and coils the reservoir 2310 about the housing 2306 to form a collapsed coiled state.

Additionally, as described in detail above, the tissue collection devices (including device 2400) can return to an expanded state by removing the collapsing force (i.e. removing a distal or coiling force) and allowing the device to recover a natural relaxed state. Alternatively, another force such as a proximal force is applied to move the device back to an expanded state. Where the collapsed state is a coiled configuration, the reservoir may need to be rotated in a counter direction to unwind the coil. For example, referring to FIG. 23*c*, if a clockwise direction winds the reservoir, then the opposing counter-clockwise direction uncoils the device.

In some cases, a separate tendon member and housing are not necessary as a guidewire lumen and guidewire can also transition the tissue collection devices between expanded and collapsed configurations. In such cases, the tendon member may be configured to function as a guidewire and the tendon housing functions as a guidewire lumen. Alternatively, the tissue collection device may have two separate structures for the guidewire and tendon member.

Additionally, where a polymer is used to form the guidewire/tendon member housing, the polymer can be melted or softened to adhere the housing to the structure of the storage reservoir or tip portion. Suitable materials include polymers, such as polyimide tubing, that can be softened or melted to adhere to the collapsible frame.

Figure 7:
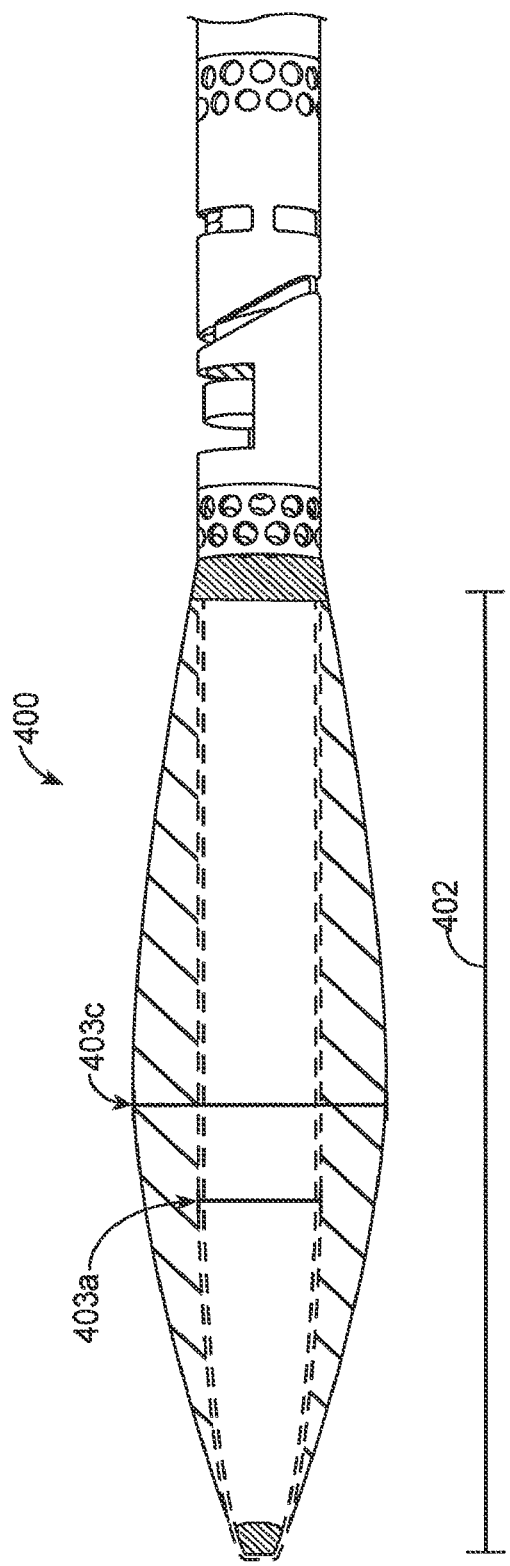
FIG. 7 is a side view of an extended configuration for a collapsible tissue collection device.

Referring to FIG. 7, the tissue collection device 400 has an additional extended configuration beyond the collapsed or expanded configurations. The extended configuration has a greater crossing profile 403*c* relative to the collapsed and expanded configurations (403*a-b*). The extended configuration may allow the device to adjust cross-sectional dimensions to efficiently pack tissue in the storage space.

Although not limiting, the tissue collection device may have the following dimensions described. In some embodiments, the minimum outer diameter is about 0.020 inches. In some embodiments, the maximum outer diameter is about 0.080 inches. In some embodiments, the device has an outer diameter between about 0.014 inches and about 0.10 inches. In further embodiments, the length of the tissue collection device (when deployed) could range from about 10 mm to about 100 mm. The outer diameter/crossing profile (when deployed) could range from about 0.02 inches to about 0.15 inches. The range of the inner diameter may follow the range of the outer diameter, differing by virtue of the wall thickness of the device.

In another aspect, the embodiments described provide for tissue collection devices that release trapped fluids and relieve fluid pressure in the storage reservoir of the devices. These devices may include venting members or venting elements through which fluid can escape and flow out of the storage reservoir. A tip portion of the device may include any suitable wall features such as holes, gaps, apertures, nets, mesh, slits, slots, etc. that accommodate the migration of fluids out of the storage reservoir. Advantageously, such embodiments, prevent the buildup of fluids in the storage reservoir, which can prevent efficient use of the available storage space. Additionally, any of the fluid releasing members or features described can be used with any of the other features described. For example, fluid releasing members can be used with a collapsible tissue collection device. Furthermore, a detachable device can include venting elements.

Figure 8:
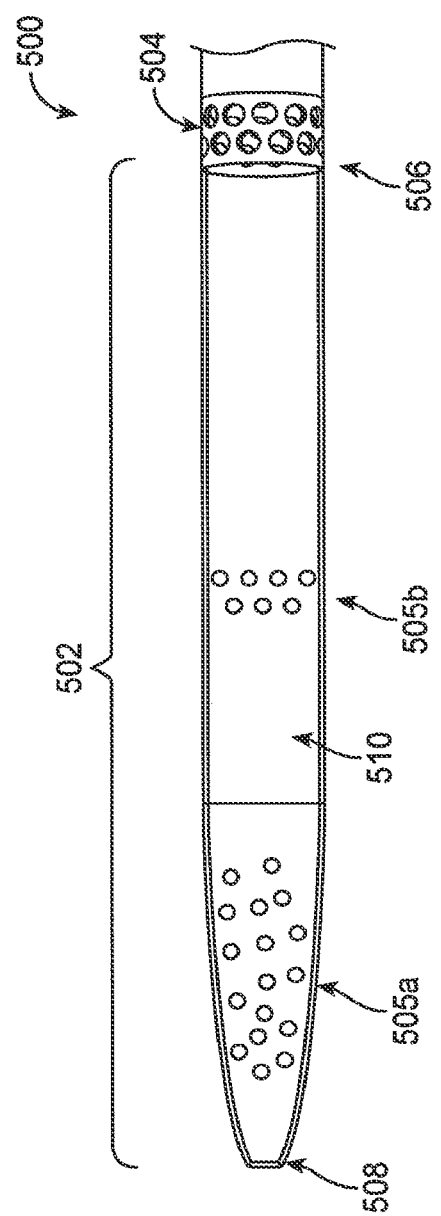
FIG. 8 is a side view of a vented tissue collection device with venting elements to release fluid pressure in the storage reservoir.

FIG. 8 shows a tissue collection device 500 with a tip portion 502. The tip portion 502 has a distal end 508 and a proximal end 506. The device 500 includes a proximal housing 504 attached to the tip portion 502. In some embodiments, the proximal housing 504 is adapted to attach or couple the device 500 to a catheter. The tip portion 502 includes a plurality of venting elements 505a at a distal end of the tip portion 502. Another set of venting elements 505b are located at another section of the tip portion 502.

The venting elements may be holes or apertures allowing fluid to escape from the tissue storage reservoir 510. This is particularly useful when tissue is packed into the storage reservoir during an atherectomy procedure where a packing mechanism such as a plunger pushes tissue distally into the storage reservoir. A pocket of fluid in the distal area of the storage reservoir can create back pressure against the plunger. As such, the trapped fluid fills valuable storage space while also impeding the storage of additional tissue.

Figure 9:
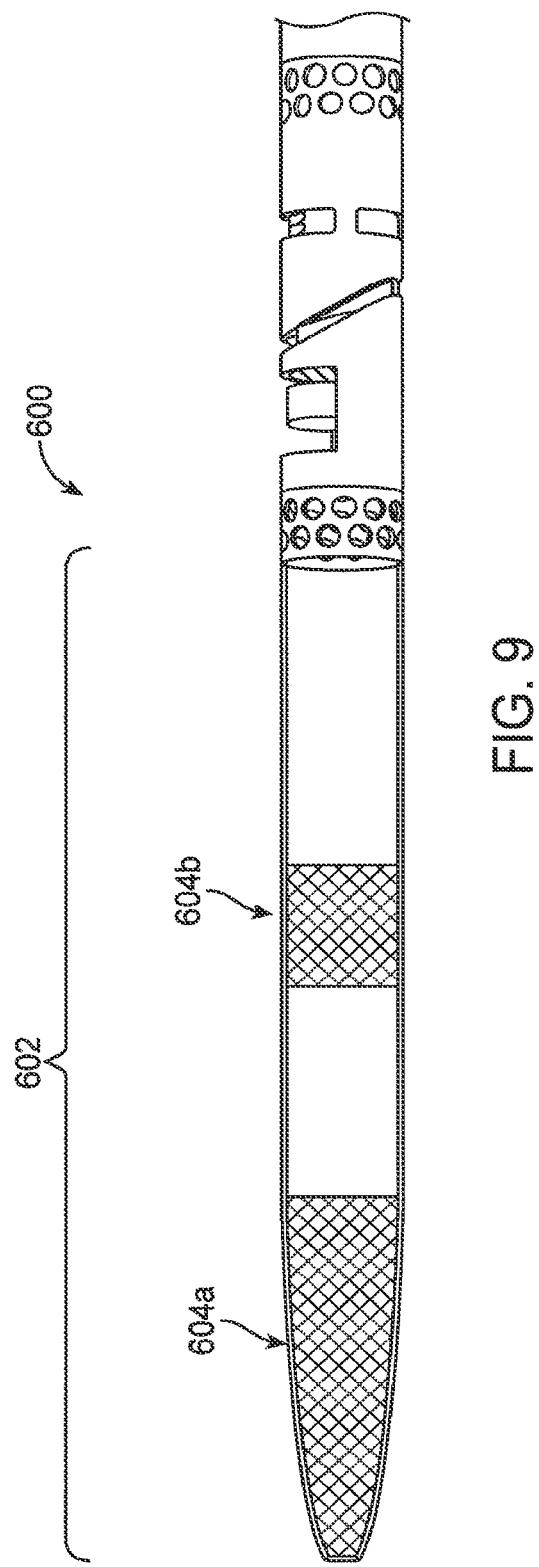
FIG. 9 is a side view of an alternative vented tissue collection device.

Although shown as apertures, the venting elements can be any suitable material or feature that allows fluid movement. FIG. 9 shows a tissue collection device 600 with a tip portion 602 having venting elements 604a-b. The venting elements are formed from a mesh net that contains solid materials within the device 600 while allowing movement of fluids out of the storage reservoir. The mesh may be made out of any suitable material including an elastic or resilient material such as shape-memory alloys, biocompatible polymers, etc. In some embodiments, the mesh is made from braided nitinol wires.

Additionally, suitable materials that can be used for the device include biocompatible alloys, metals, composites, polymers, etc. These include, but are not limited to, nitinol, PEBAX®, polyimide, PEEK, polyester, polypropylene, Tecothane®, stainless steel, elgiloy, cobalt-chromium alloys, carbon fiber, nylon, titanium and its alloys, or Kevlar. Additionally, any biocompatible material may be used to form the elastic or stretchable structure for the reservoir that can retain solids such as excised tissue while allow fluid movement out of the reservoir. In some variations, the venting elements are limited to sections of the device. Venting elements 604a-b are separated by non-venting sections of the tip portion. In such variations, the venting sections may be fused to the material of the non-venting sections. For example, the tip portion may be made from a thermoplastic polymer that can be melted and fused to the mesh to create venting elements and sections on the tip portion.

In another aspect, embodiments described provide for a tissue collection device that can be easily detached, replaced, and/or cleaned. The storage reservoirs of collection devices are often filled before a procedure is completed. Operators must then remove the treatment devices and clean the tissue collection device.

Embodiments described provide for a tissue collection device having a storage reservoir that can be detached for efficient cleaning or replacement. In some variations, the entire storage reservoir can be detached and replaced with a clean reservoir. For example, the entire tip portion may be removed and replaced with a clean tip portion. In other embodiments, a portion of the storage reservoir is removed to provide a distal opening through which stored material can be flushed out with cleaning solution (e.g. saline, water, etc.) before re-attaching the removed section.

Figure 10:
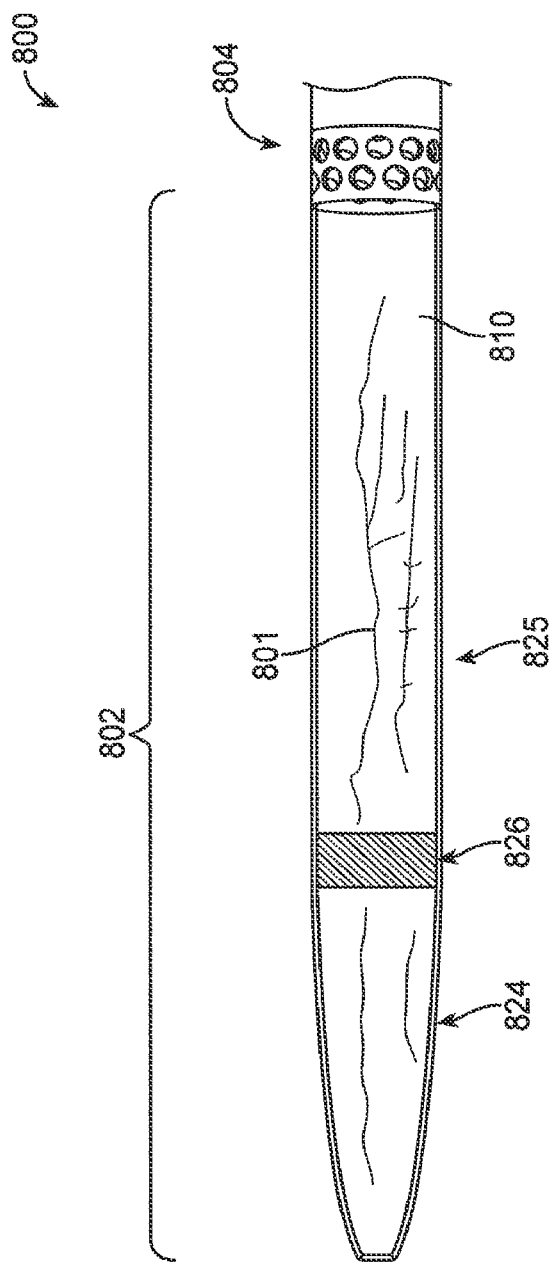
FIG. 10 is a side view of a detachable tissue collection device.

FIG. 10 shows an embodiment of the detachable tissue collection device 800 having a tip portion 802 defined by a first housing 824 and a second housing 825. The first housing 824 and the second housing 825 are detachably coupled at an attachment section 826. In some embodiments, the device 800 includes a proximal housing 804 for coupling the tissue collection device 800 to a catheter (e.g. atherectomy catheter).

Figure 11:
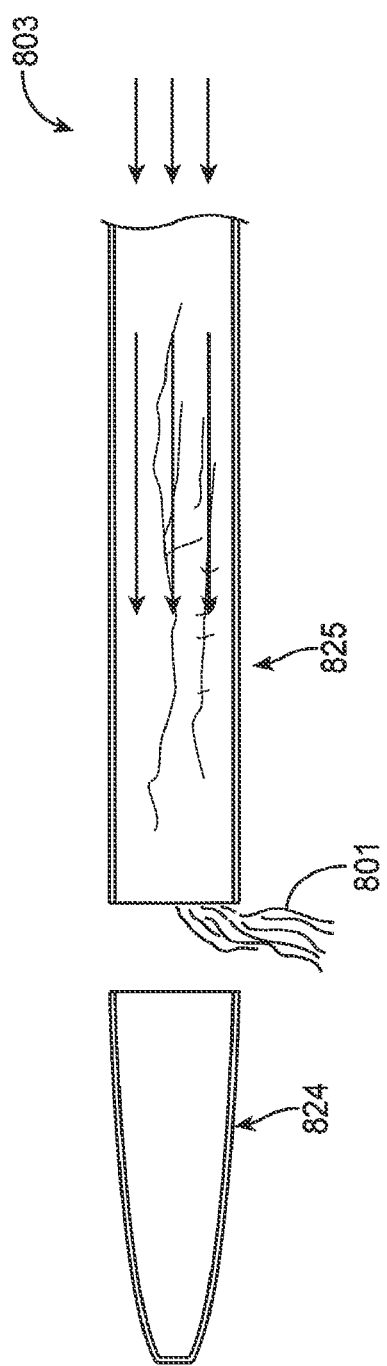
FIG. 11 shows the device of FIG. 10 with a first housing detached from a second housing of the tip portion.

The tip portion 802 defines a tissue storage reservoir 810 within the first and second housings 824, 825. The storage reservoir 810 is shown filled with stored excised material 801. To remove the material, the first housing 824 is detached from the second housing 825. Once detached, shown in FIG. 11, the two housings can be separately cleaned to remove stored material. The housings may be flushed to clear and remove debris.

In some embodiments, the storage reservoir may be limited to the volume defined between the junction 826 and the proximal housing 804. In such variations, the storage reservoir can be flushed out by cleaning the second housing 825 with cleaning fluid (e.g. saline) without flushing the first housing 824.

Figure 12:
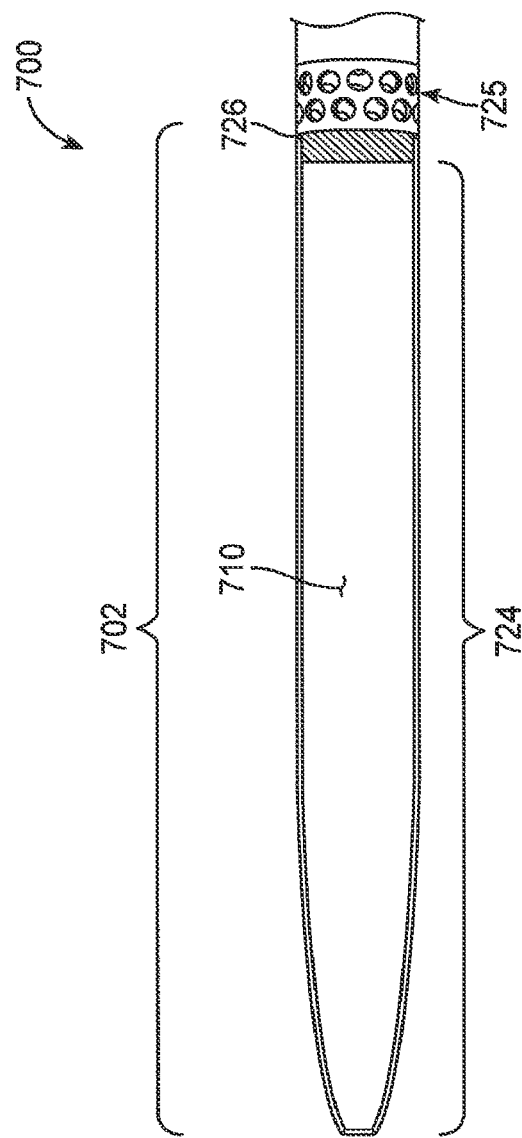
FIG. 12 is a side view of a tissue collection device with a proximal attachment section.

Alternatively, the entire tip portion may be removed for cleaning or replacement. FIG. 12 shows a tissue collection device 700 with a tip portion 702. The tip portion 702 defines a storage reservoir 710. The tip portion may be formed from a first housing 724, which also surrounds the storage reservoir 710. The first housing 724 may be coupled to a second housing or proximal housing 725. The proximal housing 725 may be connected or coupled to a catheter. In some variations, the second housing is a part of the main body of the catheter and is adapted to attach the tissue collection device to the catheter. In such cases, the tissue collection device may include an attachment element for coupling the device to the catheter via an attachment section 726.

Advantageously, because the entire tissue collection device or portions thereof are detachable, any of the removable components can be disposable such that these can be easily replaced to avoid cleaning.

Any suitable mechanism or means (e.g. friction fit, mated fit, threaded fit, hooks, securing members, etc.) may be used to detach a portion or the entirety of a tissue collection device to another device. FIGS. 13-20 illustrate examples of attachment mechanisms that can be used for this purpose.

Figure 13:
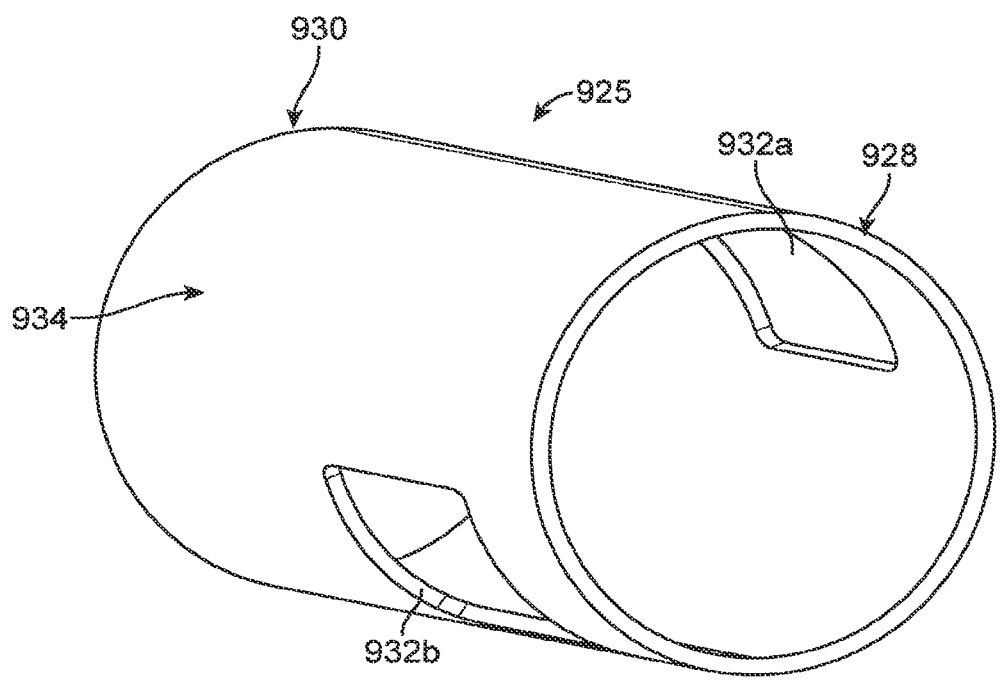
FIG. 13 is a perspective view of a second housing for a detachable tissue collection device.

FIG. 13 shows a second housing 925 with a proximal end 930 and a distal end 928. Additionally, the second housing is shown as having a generally cylindrical main body with a lumen between the proximal and distal ends. The slots or cutouts 932a-b are formed through the wall of the main body. Although shown with two slots having a generally rectangular shape, the second housing can have any number of slots with any shape. In this embodiment, the shape of the main body is designed to be inserted into a first housing shown in FIGS. 14-15.

As described above, the second housing may be a part of the tissue collection device, such as shown in FIG. 10. Alternatively, the second housing may be a part of a catheter, such as at a distal end of the catheter where the catheter attaches to a tissue collection device (see FIG. 12).

Figure 14:
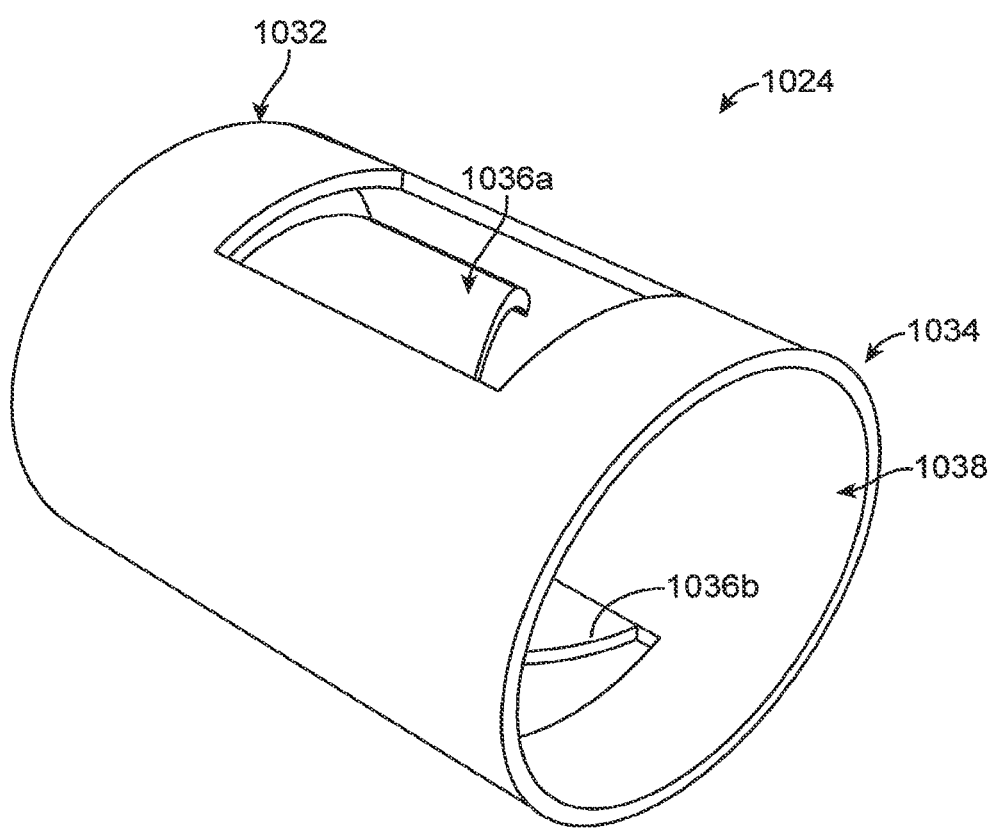
FIG. 14 is a perspective view of a first housing for a detachable tissue collection device.
Figure 15:
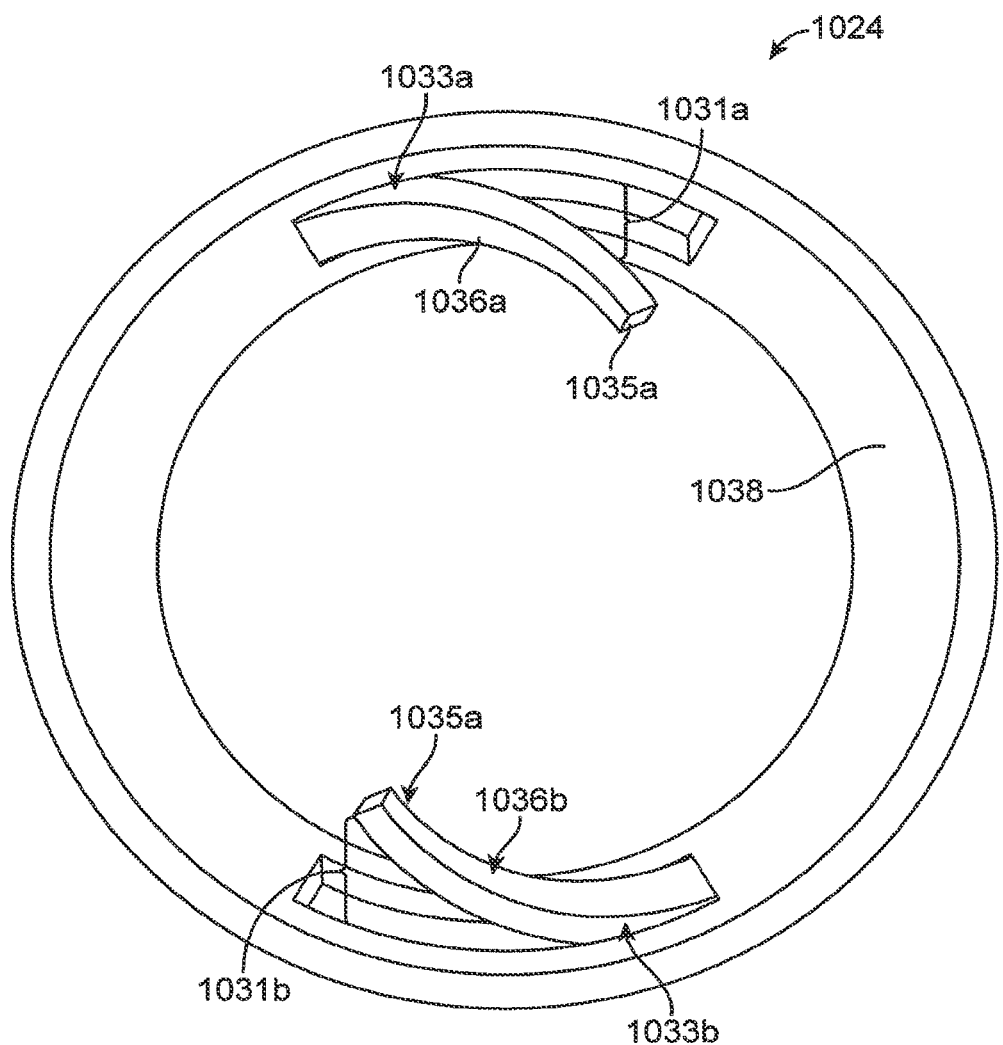
FIG. 15 shows a bottom view of the first housing shown in FIG. 14.

FIGS. 14-15 illustrate a first housing 1024 with a corresponding structure for releasably coupling to the second housing 925. As described above, the first housing may be part of the tissue collection device such as a section of the tip portion that can be removed from the rest of the tip portion. For example, the first housing may define a portion of a nosecone on a catheter such that removing the first housing exposes the remaining section of the nosecone. Alternatively, the first housing may define the entire tip portion and storage reservoir such that the entire tip portion can be removed and replaced with a clean empty storage reservoir.

As shown, the first housing has a main body with a distal end 1034 and a proximal end 1032. The first housing 1024 is shape set to the second housing such that the second housing 925 can be inserted into the first housing 1024 to form a snug fit. The first housing 1024 has an inner wall 1038 that contacts the outer wall 934 of the second housing 925 when fitted. The first housing 1024 includes protrusions shown as tabs 1036*a-b* that project from its main body towards the center. In some embodiments, the tabs 1036*a-b* protrude at an angle towards the center of the main body.

FIG. 14 shows the tabs with a proximal end 1033*a-b* that is fixed to the main body and a free end 1035*a-b* that extends toward the interior of the first housing 1024. The angled projection of the tabs creates recesses 1031*a-b* between the tabs and the inner wall 1038. Although the tabs are shown as formed from the main body of the first housing, the tabs can also be made of an separate structure or component that sits on the inner wall 1038 of the first housing 1024.

In the illustrated embodiment, the first housing 1024 has two tabs 1036*a-b* to interface and lock with the receiving slots 932*a-b* of the second housing 925. In operation, the first housing 1024 is placed over the outer wall 924 of the second housing 925 to form a snug fit. The proximal end 1032 of the first housing 1024 is advanced over the distal end 928 of the second housing 925.

Figure 16:
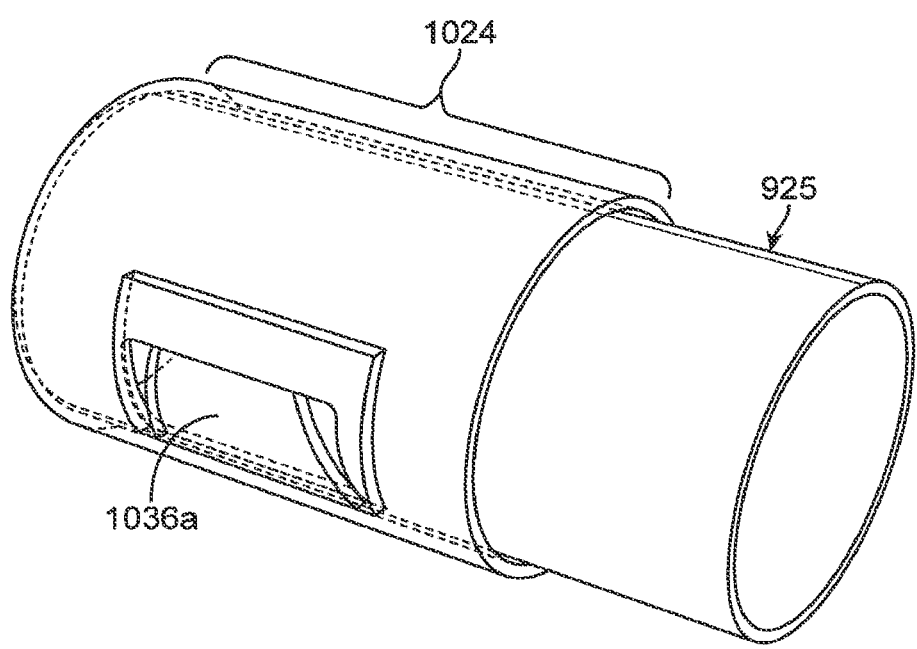
FIG. 16 shows the first and second housings of FIGS. 13-14 coupled.
Figure 17:
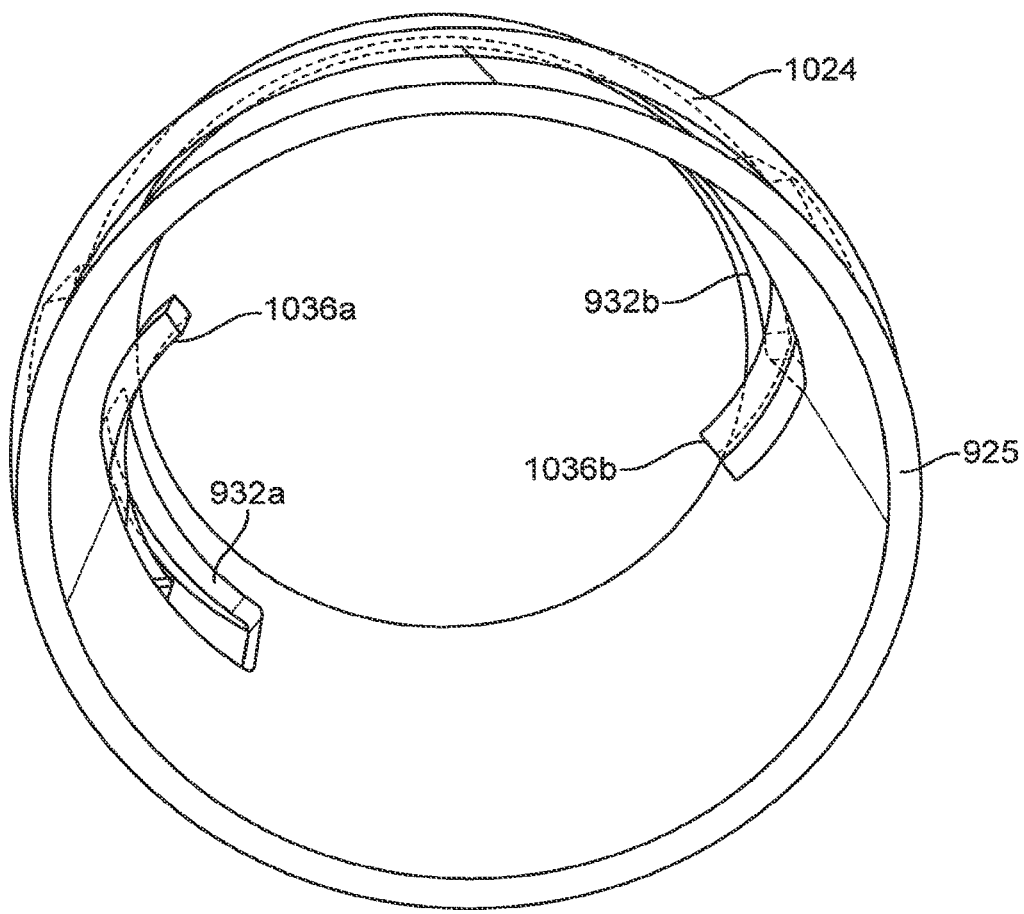
FIG. 17 shows the cross-section of the coupled housings in FIG. 16.

Then the first housing 1024 (or the second housing 925) is rotated relative to the other housing to align the tabs 1036*a-b* with the slots 932*a-b*. To lock the first and second housings, an edge of the slots 932*a-b* is slid into the recess 1031*a-b* until a portion of the main body of the second housing is held between a tab surface and the inner wall of the first housing. FIG. 16 shows the first housing 1024 surrounding the second housing 925 with tabs 1036*a-b* engaged with slots 932*a-b*. FIG. 17 shows a cross-sectional view with the first and second housing rotated to align the tabs and slots. The tabs 1036*a-b* are received through the slots 932*a-b* into an interior of the second housing 925. The edge of the slots 932*a-b* are slid into the recesses 1031*a-b* to hold and lock the lateral orientation of the second housing 925 within the first housing 1024. As shown, rotating the first housing counter-clockwise disengages the coupling structures and releases the housings from one another.

Figure 18:
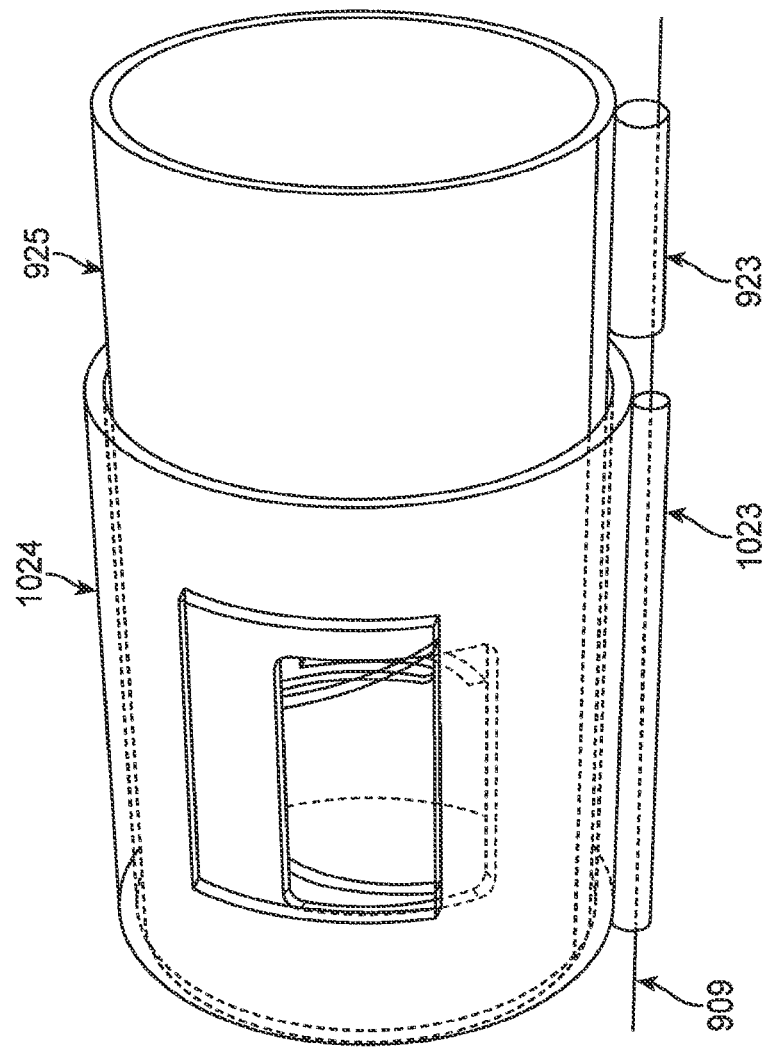
FIG. 18 is a perspective view of a pair of coupled housings with a guidewire lock.

In some variations, a locking mechanism is used to maintain the rotational orientation of the housings. FIG. 18 shows the first and second housings having a guidewire channel or lumen 1023, 923 through which a guidewire 909 can reside once the first and second housings are coupled. The guidewire prevents the housings from substantially rotating relative to one another to decouple the housings while the guidewire is in the channels.

Figure 19:
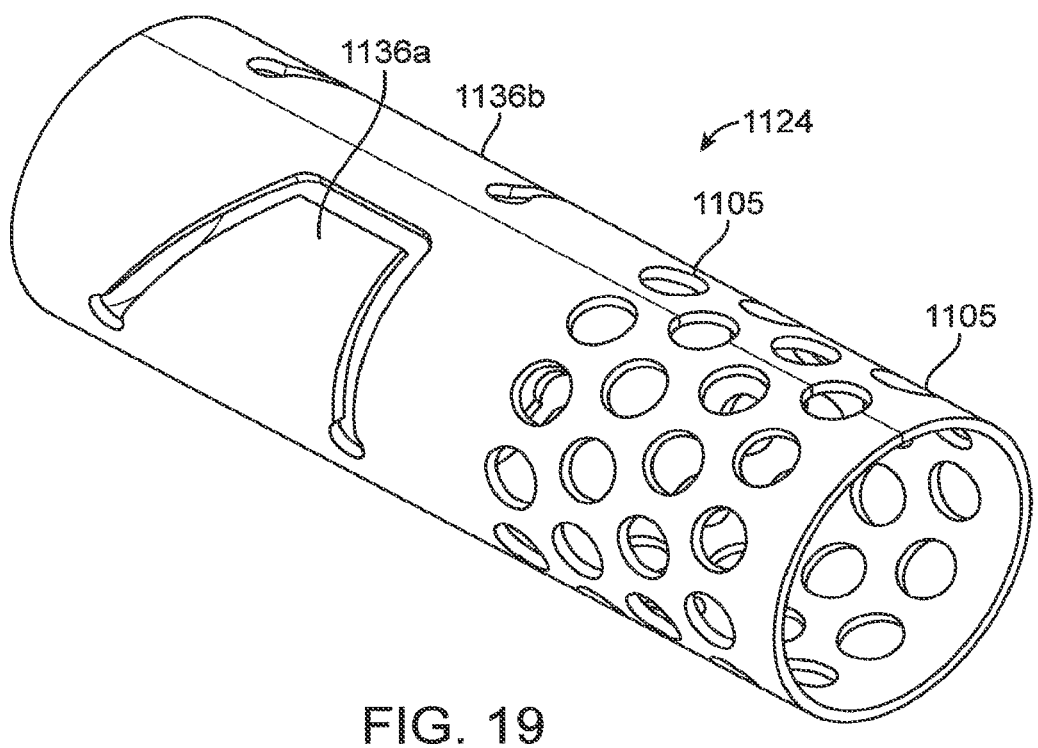
FIG. 19 is a perspective view of an alternative embodiment of the first housing.
Figure 20:
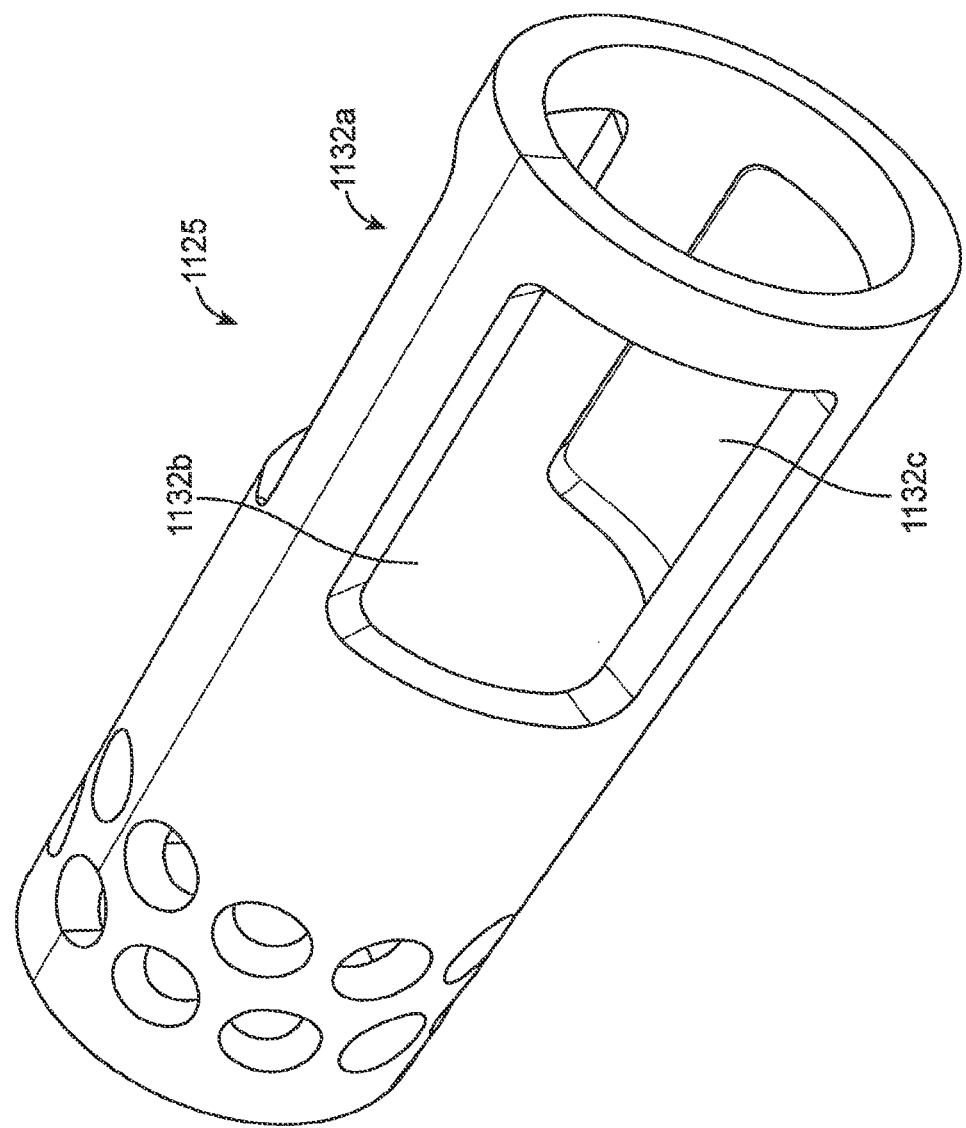
FIG. 20 is a perspective view of an alternative embodiment of the second housing.

FIGS. 19-20 show alternative embodiments of the first and second housings. FIG. 19 shows a first housing 1124 with tabs 1136*a-b* and a plurality of apertures 1105. In some embodiments, the apertures provide for fluid pressure release. FIG. 20 shows an alternative second housing 1125 having slots 1132*a-c*. Although the housings are shown with two or three tabs/slots, it is to be understood that any number of mating structures can be used to form the detachable tissue collection devices.

Additionally, any suitable materials such as nitinol, stainless steel (e.g. grade 304), or titanium or alloys may be used form the housings. Coatings including gold or platinum may be used to promote radiopacity. In some embodiments, the first housing is formed by shape setting the housing to the second housing and baking the first housing in an oven at about 504 degrees Fahrenheit for 20 minutes.

In some embodiments, second housing has an inner diameter of about 0.065 inches and an outer diameter of about 0.072 inches. The second housing may have a length of about 0.220 inches. The cutouts may have a width of about 0.050 inches and a length of about 0.070 inches. Where multiple cutouts are employed, the cutouts may be separated by a distance of about 0.025 inches.

In other embodiments, the first housing may have an inner diameter of about 0.072 inches and an outer diameter of about 0.078 inches. The first housing may have a length of about 0.230 inches.

Figure 21:
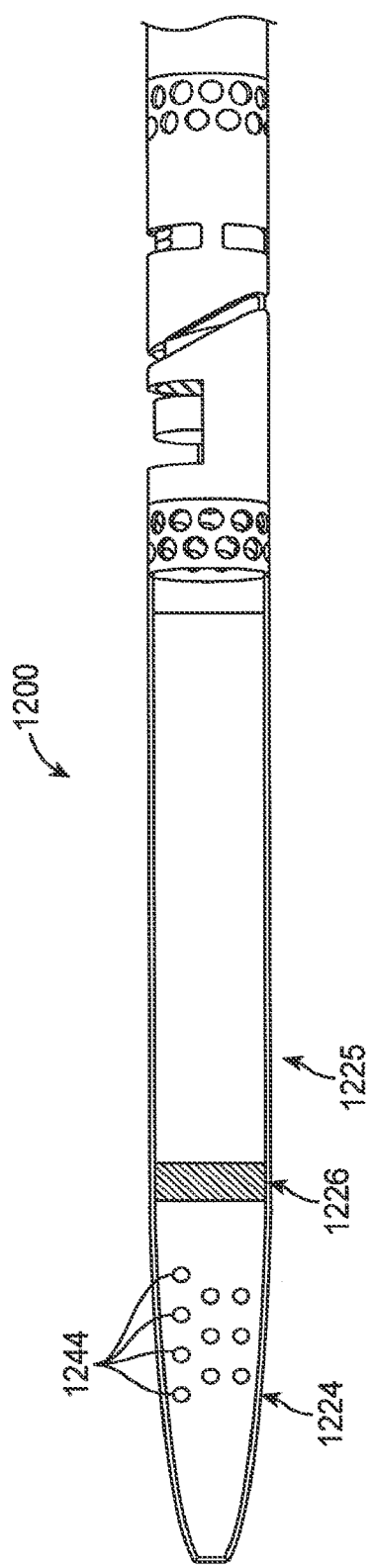
FIG. 21 is a side view of a detachable vented tissue collection device.
Figure 22:
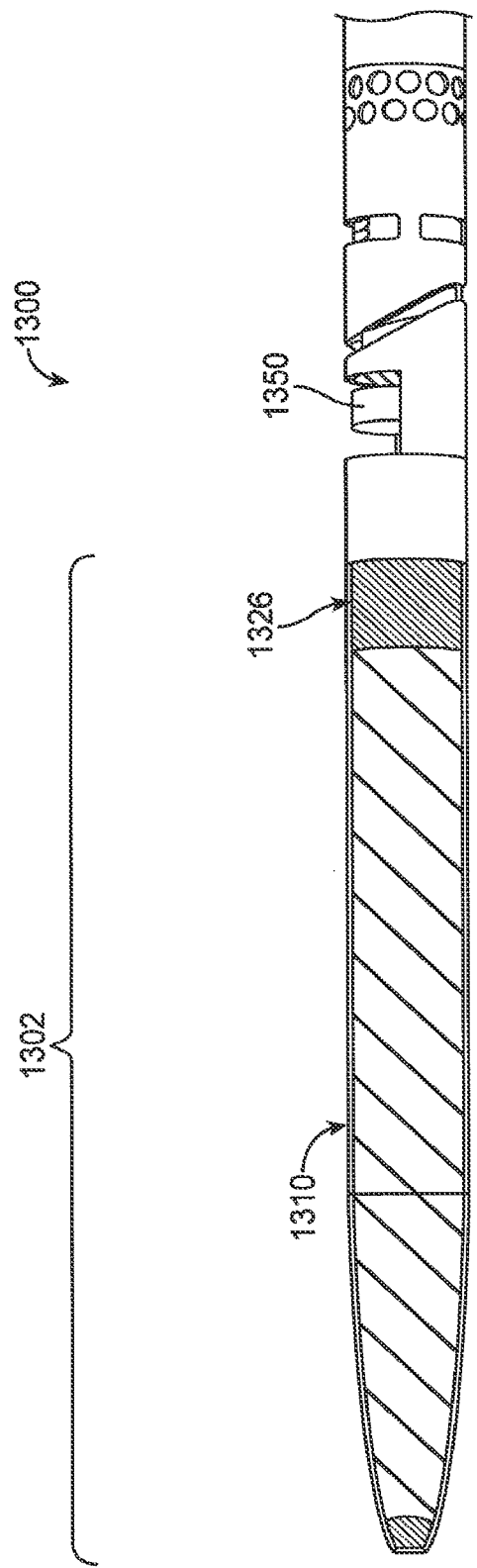
FIG. 22 is a side view of a collapsible and detachable tissue collection device.

Any of the features of the described tissue collection devices can be used in combination without departing from the disclosure. For example, FIG. 21 shows a tissue collection device having a detachable distal tip 1224. The detachable tip 1224 is attached to a tip section 1225 at an attachment point 1226. The detachable distal tip 1224 also includes venting elements 1244 for releasing fluid pressure buildup on the storage reservoir. Similarly, FIG. 22 shows a tissue collection device 1300 with a collapsible tip portion 1302. The tip portion 1302 is also releasably coupled to an atherectomy catheter at attachment section 1326.

In addition, any of the described tissue collection devices can be used with atherectomy or other occlusion crossing devices. In such cases, the atherectomy devices typically include an elongate body and a rotatable tip (with a cutter) at the first distal end of the elongate body and configured to rotate relative to the elongate body. Such devices are described in U.S. Patent Application No. 61/646,843, titled "ATHERECTOMY CATHETERS WITH IMAGING," filed on May 14, 2012, U.S. patent application Ser. No. 13/433, 049, titled "OCCLUSION-CROSSING DEVICES, IMAGING, AND ATHERECTOMY DEVICES," filed Mar. 28, 2012, U.S. patent application Ser. No. 13/175,232, titled "ATHERECTOMY CATHETERS WITH LONGITUDINALLY DISPLACEABLE DRIVE SHAFTS," filed on Jul. 1, 2011, U.S. patent application Ser. No. 12/829,277, titled "ATHERECTOMY CATHETER WITH LATERALLY-DISPLACEABLE TIP," filed on Jul. 1, 2010, and U.S. patent application Ser. No. 12/829,267, titled "CATHETER-BASED OFF-AXIS OPTICAL COHERENCE TOMOGRAPHY IMAGING SYSTEM," filed on Jul. 1, 2010. All of the above are herein incorporated by reference in their entirety.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative"

limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A tissue collection device comprising:
   a proximal end and a distal end defining a length of the device;
   a shaft located along at least a portion of the length, the shaft defining a lumen;
   a tendon member residing in the shaft lumen; and
   a tissue storage reservoir having an adjustable cross-section, wherein the tissue storage reservoir is movable between a first configuration and a second configuration, the second configuration having a smaller crossing profile and a reduced cross-section relative to the first configuration,
   wherein the proximal end is adapted to couple to a catheter and further comprises an opening configured to communicate with the catheter when the catheter is coupled thereto such that excised tissue from the catheter can enter the tissue storage reservoir, and
   wherein the tissue storage reservoir comprises a plurality of gaps having a width from 50 µm to 200 µm.

2. The device of claim 1, wherein the tissue storage reservoir is configured to compress when moved to the second configuration and expand when moved to the first configuration.

3. The device of claim 1, wherein the tissue storage reservoir comprises a mesh, the mesh configured to collapse when the tissue storage reservoir is moved from the first configuration to the second configuration.

4. The device of claim 1, wherein the tissue storage reservoir comprises a wire frame that is configured to collapse when the tissue storage reservoir moves from the first configuration to the second configuration.

5. The device of claim 1, wherein the tissue storage reservoir is formed from a braided nitinol mesh that is configured to collapse and expand between the first and second configurations.

6. The device of claim 1, wherein the tissue storage reservoir comprises an elastic material.

7. The device of claim 1, wherein the tissue storage reservoir comprises a resilient material.

8. The device of claim 1, wherein the tissue storage reservoir comprises a shape-memory material.

9. The device of claim 1, wherein the tissue storage reservoir is configured to move from the first configuration to the second configuration by applying a distally directed force along a longitudinal axis of the device.

10. The device of claim 9, wherein the distally directed force is applied to the distal end of the device.

11. The device of claim 1, wherein the tissue storage reservoir is configured to move from the first configuration to the second configuration by extending the length of the device.

12. The device of claim 1, further comprising a guidewire lumen and a guidewire residing in the guidewire lumen, wherein distally moving the guidewire against the distal end of the device applies a distally directed force to thereby move the tissue storage reservoir from the first configuration to the second configuration.

13. The device of claim 12, wherein the tissue storage reservoir is configured to return to the first configuration from the second configuration after the distal force is released.

14. The device of claim 12, wherein the tissue storage reservoir is configured to return to the first configuration from the second configuration by applying a proximally directed force at the distal end.

15. The device of claim 1, wherein the first configuration has a crossing profile of 0.080 inches.

16. The device of claim 1, wherein the second configuration has a crossing profile of 0.020 inches.

17. The device of claim 1, wherein the length is from 10 mm to 100 mm.

18. The device of claim 1, wherein a crossing profile of the tip portion is from 0.020 inches to 0.080 inches.

19. The device of claim 1, wherein the tissue storage reservoir comprises a porous member configured to allow fluid movement out of the storage reservoir.

20. The device of claim 1, the tissue storage reservoir further comprising a third configuration, the third configuration having a greater crossing profile relative to the first configuration.

21. The device of claim 1, wherein the tissue storage reservoir is adapted to be biased towards the first configuration.

22. The device of claim 1, wherein the device is configured such that distally moving the tendon member against a distal end of the device applies a distally directed force to thereby move the tissue storage reservoir from the first configuration to the second configuration.

23. The device of claim 22, wherein the device is configured such that proximally moving the tendon member moves the tissue storage reservoir from the second configuration to the first configuration.

24. The device of claim 1, wherein the tissue storage reservoir has a distal end and a proximal end, and the distal end of the tissue storage reservoir is fixed to the tendon member and the proximal end of the tissue storage reservoir is fixed to the shaft.

25. The device of claim 24, wherein the tissue storage reservoir is adapted to transition to the second configuration by distally moving the tendon member relative to the shaft.

26. The device of claim 24, wherein the tissue storage reservoir is adapted to transition to the second configuration by rotating the tissue storage reservoir about the shaft to form a coiled collapsed configuration.

27. The device of claim 24, wherein the tissue storage reservoir comprises a resilient frame configured to naturally return to the first configuration.

28. A tissue collection device comprising:
a proximal end and a distal end defining a length of the device;
a shaft located along at least a portion of the length, the shaft defining a lumen;
a tendon member residing in the shaft lumen; and
a tissue storage reservoir having an adjustable cross-section, wherein the tissue storage reservoir is movable between a first configuration and a second configuration, the second configuration having a smaller crossing profile and a reduced cross-section relative to the first configuration,
wherein the proximal end is adapted to couple to a catheter, and wherein the proximal end further comprises an opening configured to communicate with the catheter when the catheter is coupled thereto such that excised tissue from the catheter can enter the tissue storage reservoir, and
wherein the tissue storage reservoir comprises a plurality of gaps of between 0.01 mm to 0.5 mm.

* * * * *